United States Patent [19]

Ozaki

[11] Patent Number: 5,661,560
[45] Date of Patent: Aug. 26, 1997

[54] ELLIPTICAL LIGHT MEASURING METHOD

[75] Inventor: Yoshiharu Ozaki, Kanagawa, Japan

[73] Assignee: Nippon Telegraph and Telephone Public Corporation, Japan

[21] Appl. No.: 654,595

[22] Filed: May 29, 1996

Related U.S. Application Data

[62] Division of Ser. No. 293,130, Aug. 19, 1994, Pat. No. 5,548,401.

[30] Foreign Application Priority Data

| Aug. 23, 1993 | [JP] | Japan | 5-207480 |
| Aug. 23, 1993 | [JP] | Japan | 5-208072 |
| Nov. 17, 1993 | [JP] | Japan | 5-288275 |
| Dec. 1, 1993 | [JP] | Japan | 5-301448 |
| Mar. 9, 1994 | [JP] | Japan | 6-038081 |
| Mar. 9, 1994 | [JP] | Japan | 6-038083 |

[51] Int. Cl.[6] ................................... G01J 4/00
[52] U.S. Cl. ...................... 356/364; 356/366; 356/367; 250/225
[58] Field of Search ............... 356/364, 366–367; 250/225

[56] References Cited

U.S. PATENT DOCUMENTS

| 4,740,078 | 4/1988 | Daendliker et al. | 356/367 |
| 4,810,089 | 3/1989 | Murakoshi et al. | 356/367 |
| 4,973,163 | 11/1990 | Sakai et al. | 356/367 |
| 5,037,202 | 8/1991 | Batchelder et al. | 356/364 |

OTHER PUBLICATIONS

A.P. Gosh and D.B. Dove, "Direct Phase Measurements in Phase Shift Masks", SPIE vol. 1673 Integrated Circuit Metrology, Inspection, and Process Control/ VI (1991), pp. 242–254.

Stanley S.C. Chim and Fordon S. Kino, "Phase measurements using the Mirau Correlation Microscope", Jun. 1, 1991 / vol. 30 No. 16 / Applied Optics, pp. 2197–2201.

Wolfgang Budde, "Photoelectric Analysis of Polarized Light", May 1962 / vol. 1, No. 3 / Applied Optics, pp. 201–205.

Emi Tamechika et al. "Investigation of Single Sideband Optical Lithography (SSBL) Using Oblique Incidence Illumination", EIPB 1992 Orlando, The 36th Int'l Symposium on Electron, Ion and Photon Beams / May 26–29, 1992, 3 pages.

Takahiro Ode, "Improvement of Phase Measurements in Phase–Shift Masks with a Differential Heterodyne Interferometer", PhotoMask Japan, Digest of Papers Photomask Japan 1994, Symposium on Photomask and X–Ray Mask Technology, Apr. 22, 1994, Kanagawa Science Park Kanagawa, Japan, 3 pages.

Matsuura et al. "Measurement of optical phase difference using a polarization technique" Optics and Laser Technology, Dec. 1977, vol. 9, No. 2, pp. 285–289.

*Primary Examiner*—Frank G. Font
*Assistant Examiner*—Jason D. Vierra Eisenberg
*Attorney, Agent, or Firm*—Samuels, Gauthier, Steven & Reppert

[57] ABSTRACT

In a photomask inspecting method, a photomask is inspected on the basis of the difference between the polarized state of elliptical light produced upon superposition of two linearly polarized light beams having orthogonal polarization directions and passing through two different optical paths and the polarized state of elliptical light produced when two linearly polarized light beams are superposed on each other after a target portion of a photomask is set in the optical path of one of the linearly polarized light beams. A photomask inspecting apparatus is also disclosed.

1 Claim, 20 Drawing Sheets

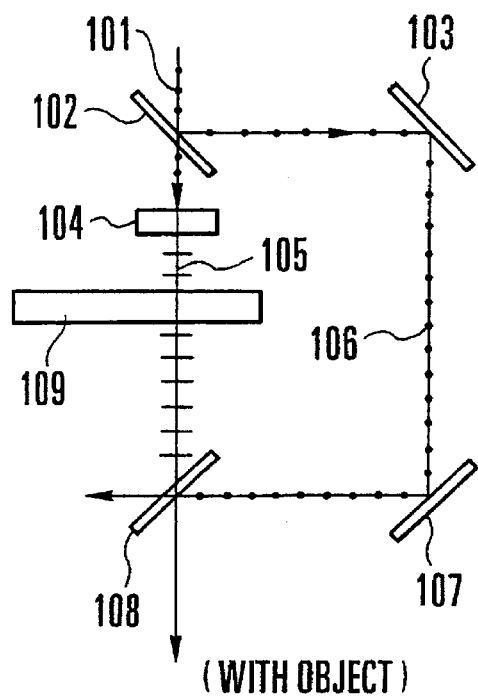
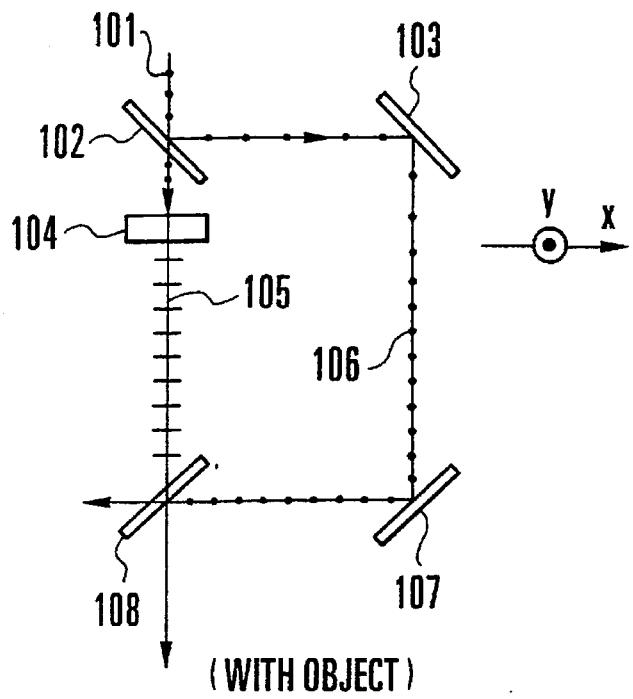
FIG.1A  FIG.1B
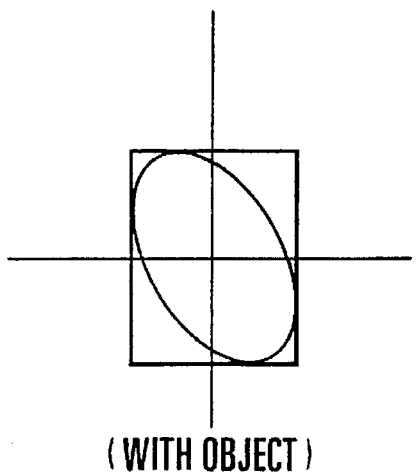
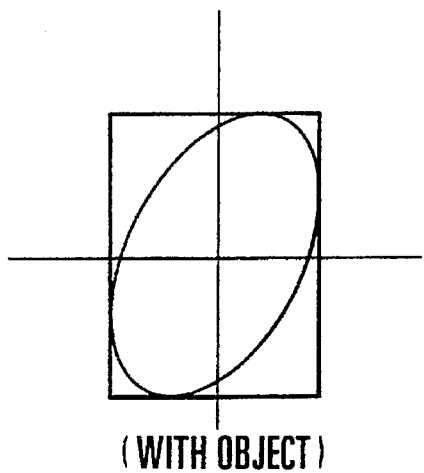
FIG.1C  FIG.1D

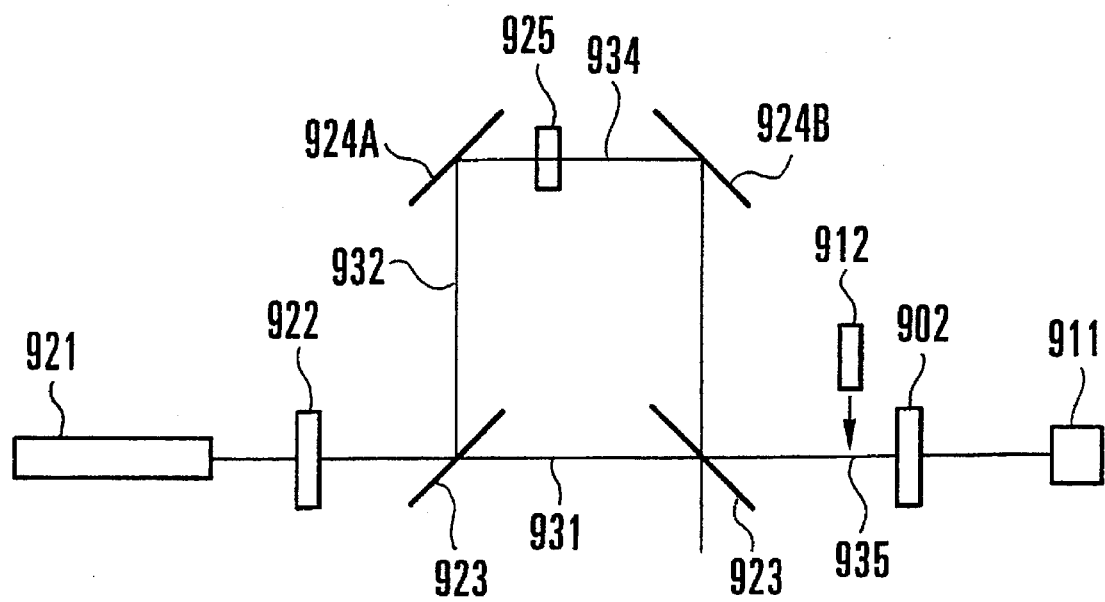
F I G. 13
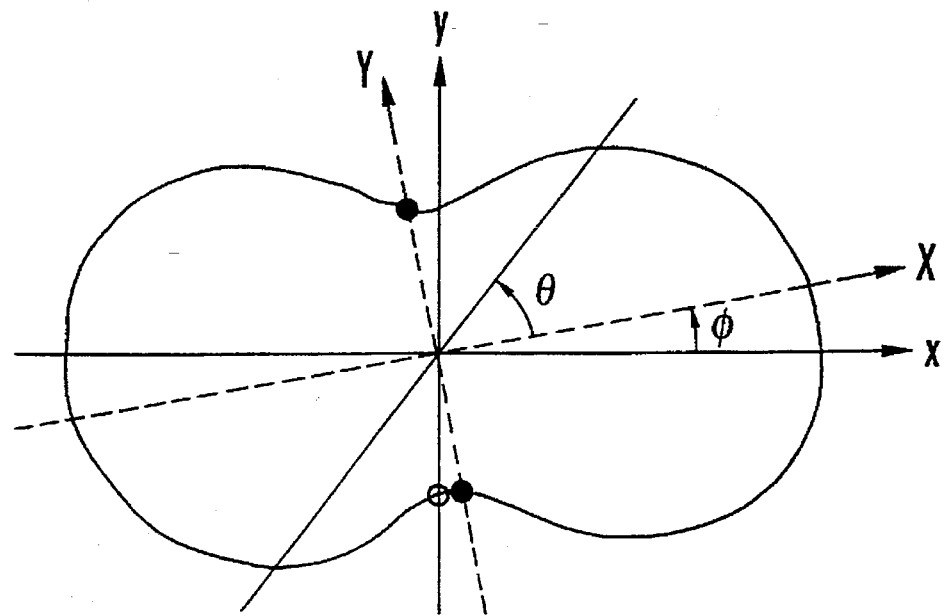
F I G. 14

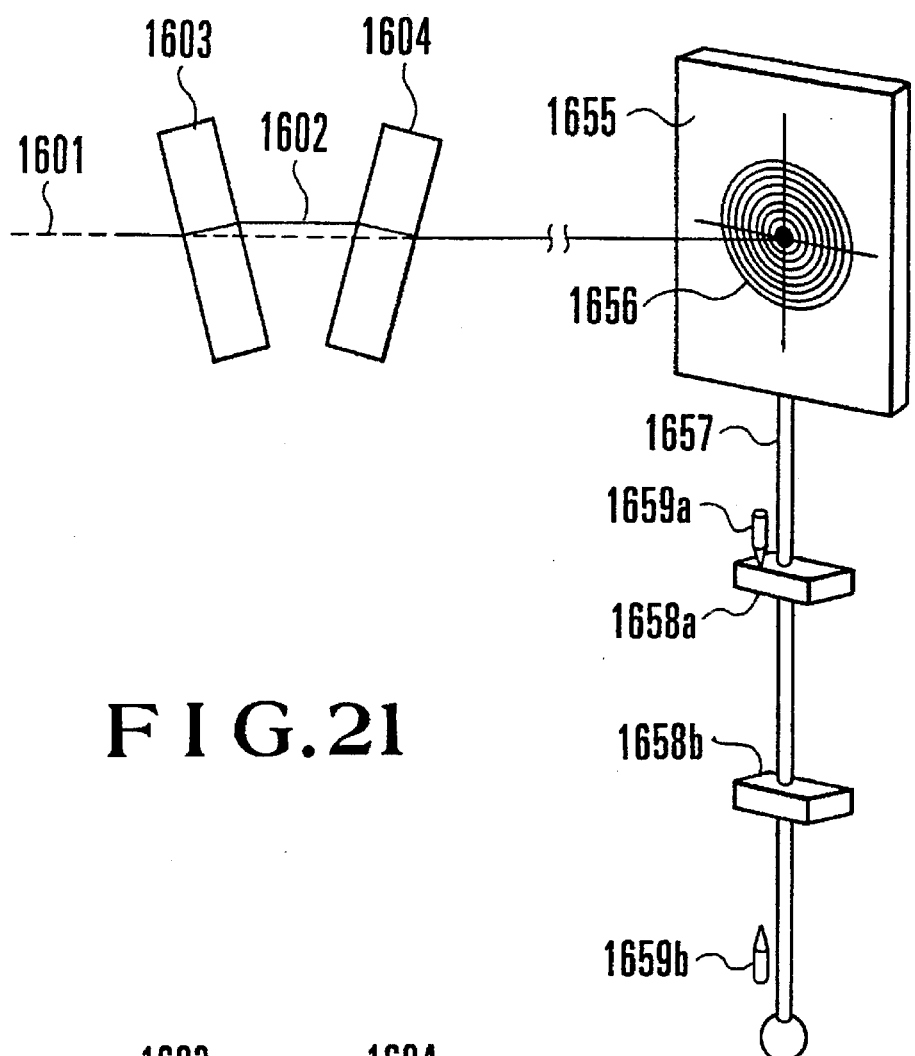
F I G. 21
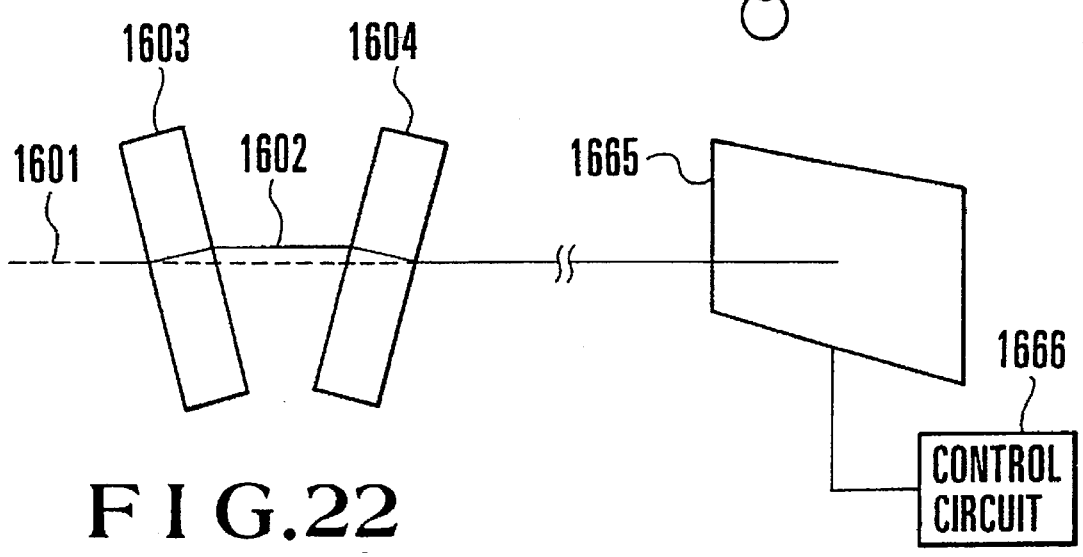
F I G. 22

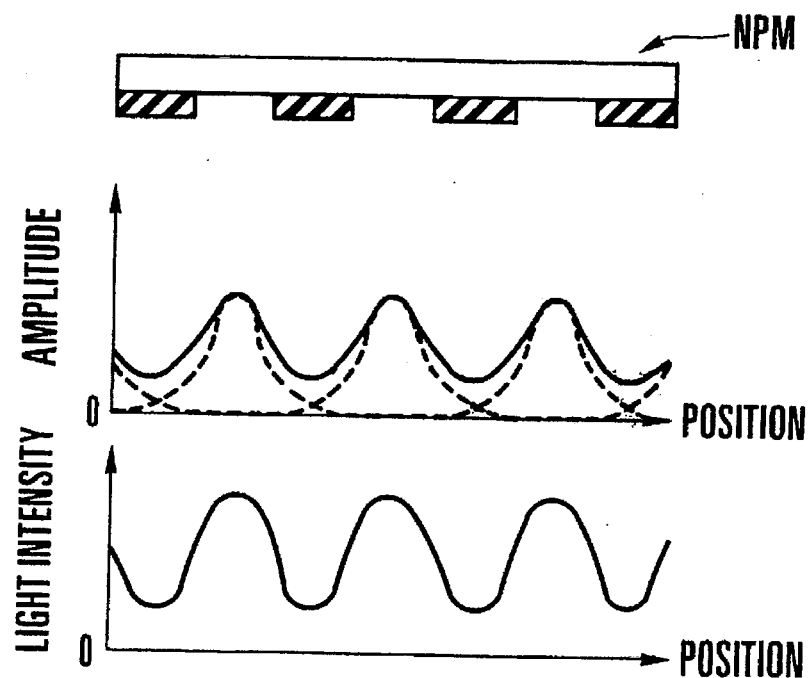
F I G. 26A
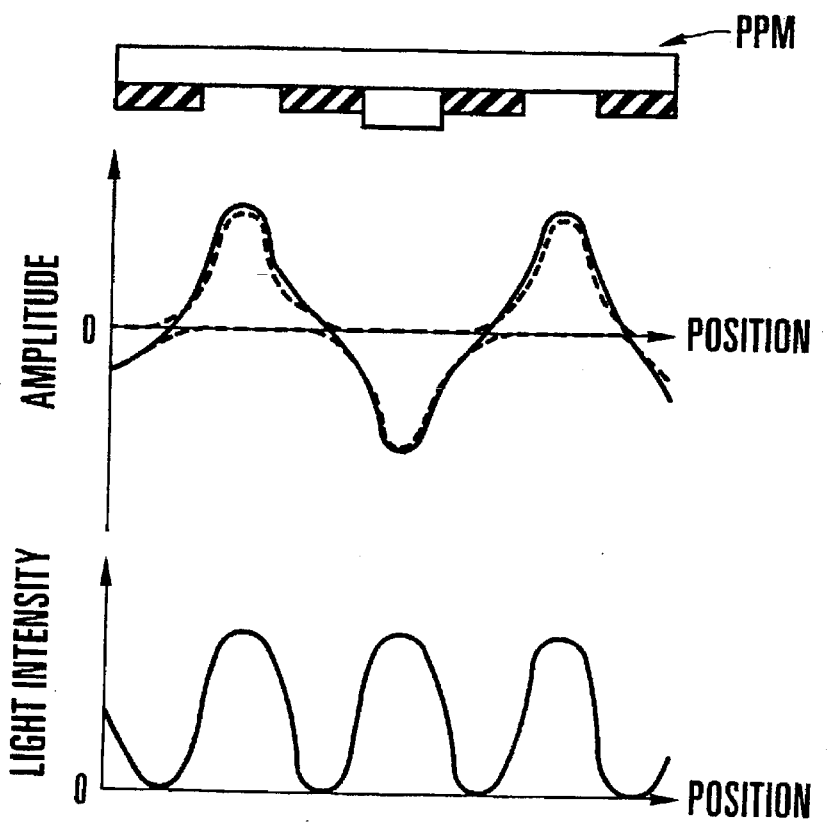
F I G. 26B

ELLIPTICAL LIGHT MEASURING METHOD

This is a divisional of application Ser. No. 08/293,130 filed on Aug. 19, 1994 U.S. Pat. No. 5,548,401.

BACKGROUND OF THE INVENTION

The present invention relates to a photomask inspecting method and apparatus.

Recently, in order to increase the integration degree of semiconductor integrated circuits, various micropatterning techniques have been proposed. In general, lithography is used for patterning. In order to form micropatterns, the resolution power of a reduction projection exposure apparatus (called a stepper) used for lithography must be increased. A technique of increasing the numerical aperture of a projection lens and decreasing the wavelength of a light source has been employed to increase the resolution power of this reduction projection exposure apparatus. This technique, however, has already achieved a resolution power close to its theoretical limit. For this reason, studies have recently been made to use other techniques to increase the resolution power.

Methods of overcoming the above theoretical limit include a method of giving a phase difference of nearly 180° to light passing through a transparent portion of a patterned photomask in processing the photomask, and a method of giving a certain degree of transparency and a phase change to a pattern portion. These photomasks are generally called phase shift masks. Such a method is disclosed in, e.g., J4 of Proceedings of The 36th International Symposium on Electron, Ion and Photon Beams.

This technique is a technique of improving a light intensity distribution on an image surface as a result of interference of light from each portion of a photomask. A phase shift technique will be described below in comparison with a technique using a normal photomask.

FIG. 26A shows amplitude and light intensity distributions obtained by performing image formation using a normal photomask NPM using a line-and-space pattern formed by selectively placing mask members on a glass substrate. In the amplitude distribution characteristics shown in FIG. 26A, the dotted lines represent the amplitude distribution of transmitted light from the respective spaces, and the solid line represents the amplitude distribution as a result of interference. The light intensity distribution is obtained by squaring the amplitude distribution represented by the solid line.

FIG. 26B shows amplitude and light intensity distributions obtained by using a phase shift photomask PPM. Similar to FIG. 26A, the dotted lines represent the amplitude distribution of transmitted light from the respective spaces, and the solid line represents an amplitude distribution as a result of interference. The light intensity distribution is obtained by squaring the amplitude distribution represented by the solid line.

In the normal photomask NPM shown in FIG. 26A, since diffracted light beams from adjacent transparent portions are superposed in phase, the light intensity of each light-shielding portion does not become 0. In contrast to this, in the phase shift photomask PPM shown in FIG. 26B, since diffracted light beams from adjacent transparent portions are superposed in opposite phases, the light intensity of each light-shielding portion becomes 0. As a result, with the phase shift photomask PPM shown in FIG. 26B, the contrast of an image is improved. Note that the contrast improving effect is reduced as the phases of light beams from adjacent transparent portions shift from K, and the amplitude of light transmitted through a phase shift member decreases because of absorption in the phase shift member.

In a phase shift mask, therefore, it is very important to control the phase and amplitude transmittance of transmitted light from each portion. If the refractive index and extinction coefficient of each material used for a photomask are accurately obtained, a phase, an amplitude transmittance, and an energy transmittance can be controlled by controlling the thickness of each material.

In many cases, however, it is difficult to accurately measure the refractive index and extinction coefficient of each material. In addition, impurities are mixed in each material in the manufacturing process to cause errors in the refractive index and the extinction coefficient. Furthermore, the thickness of each material is inevitably accompanied by a manufacturing tolerance.

For this reason, a phase, an amplitude transmittance, and an energy transmittance are actually measured with respect to each portion of a manufactured photomask, and the results are fed back to the manufacturing process. These operations are repeated to realize a desired photomask. However, no effective means for measuring a phase, an amplitude transmittance, and an energy transmittance is available.

SUMMARY OF THE INVENTION

It is an object of the present invention to provide a photomask inspecting method and apparatus which can easily and accurately observe or measure a phase, an amplitude transmittance, and an energy transmittance.

In order to achieve the above object, according to the present invention, light is split into light beams passing through two different optical paths, and the two light beams are converted into linearly polarized light beams in polarization directions perpendicular to each other within a plane perpendicular to the propagating direction of the light. In addition, the polarized state of elliptical light produced upon superposition of the two linearly polarized light beams is observed. Thereafter, a target portion (to be inspected) of a photomask is set in one of the optical paths, and the polarized state of elliptical light produced upon setting of this target portion is observed. The photomask is inspected by observing the polarized state of light produced upon superposition, which changes before and after the target portion of the photomask is set in the optical path.

With this operation, the amplitude transmittance and energy transmittance of each photomask portion, and a phase change amount upon transmission of light trough each photomask portion can be obtained by observing the polarized state of elliptical light produced upon superposition of linearly polarized light beams perpendicular to each other. This principle will be described below with reference to FIGS. 1A to 1D.

FIGS. 1A and 1B show an optical system in the present invention. FIG. 1A shows a case wherein an object to be inspected is located in one of the optical paths of linearly polarized light beams perpendicular to each other. FIG. 1B shows a case wherein the object is not located in the optical path. Referring to FIGS. 1A and 1B, the propagating direction of light is set within a plane parallel to the drawing surface. In addition, the x-axis is set in the right direction on the drawing surface, and the y-axis is set in the direction from the lower surface side to the upper surface side of the drawing. Referring to FIGS. 1A and 1B, reference numeral 101 denotes light linearly polarized in advance to oscillate in the y-axis direction; 102, a half mirror for splitting the light 101 into two light beams; 103, a total reflection mirror for bending the optical path of one of the light beams; 104, a λ/2 plate; 105, a linearly polarized light beam in which a target portion of a photomask will be inserted; and 106, a linearly polarized light beam passing through the other optical path. The linearly polarized light beam 106 oscillates in the y-axis direction, and the linearly polarized light beam 105 oscillates in the x-axis direction. The two linearly polarized light beams 105 and 106 are superposed on each other via the total reflection mirror 107 and the half mirror 108. FIGS. 1C and 1D show polarized states within a plane perpendicular to the propagating direction of light, which states are obtained by using the optical system shown in FIGS. 1A and 1B.

If the linearly polarized light beams 105 and 106 are expressed as $$E_x = a_x \cos(\omega t - \delta_1) \quad (1)$$

$$E_y = a_y \cos(\omega t - \delta_2) \quad (2)$$

where $E_x$ is the linearly polarized light beam oscillating in the x-axis direction at a given point closer to the propagating direction than the half mirror 108 before a photomask 109 is inserted, $E_y$ is the linearly polarized light beam oscillating in the y-axis direction at the same point as that defining $E_x$, $a_x$ is the amplitude of $E_x$, $a_y$ is the amplitude of $E_y$, $\delta_1$ is the initial phase of $E_x$, and $\delta_2$ is the initial phase of $E_y$, then light produced upon superposition of the two light beams is represented by $$\frac{E_x^2}{a_x^2} + \frac{E_y^2}{a_y^2} - \frac{2 E_x \cdot E_y}{a_x \cdot a_y} = \sin^2\delta \quad (3)$$

For $$\delta = \delta_1 - \delta_2 \quad (4)$$

When the photomask 109 to be inspected is inserted in the optical path of the linearly polarized light beam 105 in the x-axis direction, as shown in FIG. 1A, $$E_x' = a_x' \cos(\omega t - \delta_1') \quad (5)$$

where $E_x'$ is the linearly polarized light beam oscillating in the x-axis direction at the same point defining $E_x$ after the photomask 109 is inserted, $\delta_1'$ is the value obtained by changing 61 upon insertion of the photomask 109, and $a_x'$ is the value obtained by changing $a_x$ upon insertion of the photomask 109. The light produced upon superposition of the two light beams can be represented by $$\frac{(E_x')^2}{(a_x')^2} + \frac{E_y^2}{a_y^2} - \frac{2 E_x' E_y}{a_x' a_y} \cos\delta' = \sin^2\delta' \quad (6)$$

For $$\delta' = \delta_1' - \delta_2 \quad (7)$$

According to the basic principle of the present invention, therefore, elliptical light produced upon superposition of two linearly polarized light beams before insertion of the photomask 109 is observed or measured first to obtain $a_x$ and $\delta$. Thereafter, elliptical light produced upon superposition of two linearly polarized light beams after insertion of the photomask 109 is observed or measured to obtain $a_x'$ and $\delta'$.

Letting θ be the phase change amount introduced by the photomask 109, t be the amplitude transmittance, and T be the energy transmittance, $$\theta = \delta' - \delta \quad (8)$$

$$t = a_x'/a_x \quad (9)$$

$$T = (a_x'/a_x)^2 \quad (10)$$

Thus, these values can be obtained.

BRIEF DESCRIPTION OF THE DRAWINGS

FIG. 1A is view for explaining the principle of the present invention and a state wherein two linearly polarized light beams propagate, showing an optical system including an object to be inserted;

FIG. 1B is a view for explaining the principle of the present invention and a state wherein two linearly polarized light beams propagate, showing the optical system including no object to be inspected;

FIG. 1C is a view showing the polarized state of light, produced upon superposition of two light beams, within a plane perpendicular to the propagating direction of the light when the object is present, as shown in FIG. 1A;

FIG. 1D is a view showing the polarized state of light, produced upon superposition of two light beams, within a plane perpendicular to the propagating direction of the light when the object is not present, as shown in FIG. 1B;

FIG. 13 is a view showing an embodiment of a measurement system based on the principle shown in FIG. 11;

FIG. 14 is a view showing a measurement result obtained by measuring elliptical light using the measurement system in FIG. 13;

FIGS. 20, 21, and 22 are views showing embodiments of an optical path adjusting apparatus of the present invention;

FIG. 26A is a graph showing amplitude and light intensity distributions obtained by using a normal photomask NPM; and FIG. 26B is a graph showing amplitude and light intensity distributions obtained by using a phase shift photomask PPM.

DESCRIPTION OF THE PREFERRED EMBODIMENTS

Figure 2:
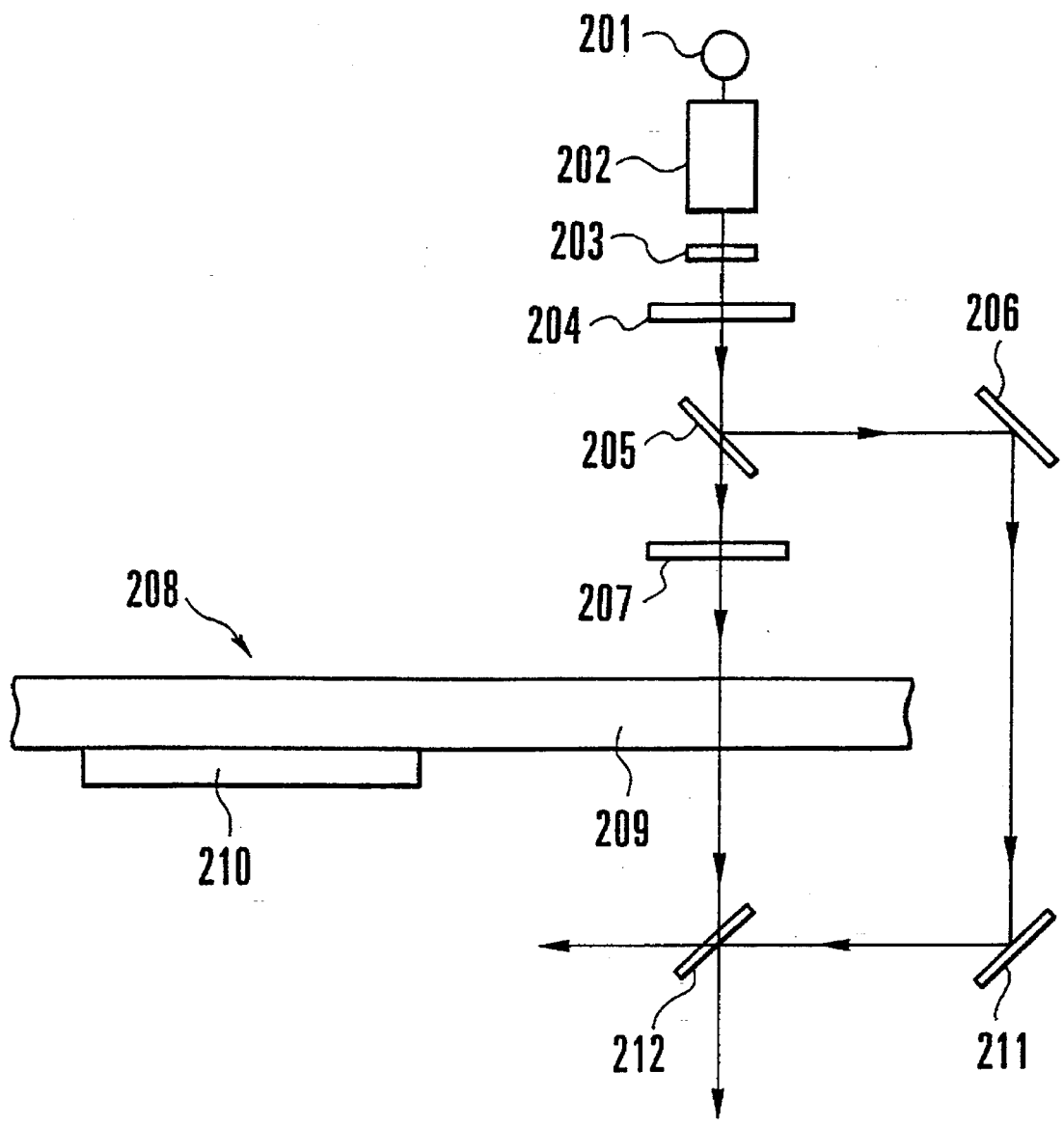
FIG. 2 is a view showing the system configuration of an embodiment of the present invention.

FIG. 2 shows an embodiment of the present invention. Referring to FIG. 2, reference numeral 201 denotes a light source such as a low-pressure mercury lamp used for lithography; 202, an optical system having focusing and collimating functions; 203, a filter for extracting monochromatic light such as a g- or i-line from light emitted from the light source 201; 204, a linear polarizer; 205, a half mirror; 206 and 211, total reflection mirrors; and 207, a $\lambda/2$ plate. Light emitted from the light source 201 is converted into monochromatic light, collimated, and linearly polarized by the optical system 202, the filter 203, and the linear polarizer 204. This linearly polarized light is amplitude-split into two light beams by the half mirror 205. One light beam propagates straight, and its oscillating direction is rotated through 90° by the $\lambda/2$ plate 207. The other light beam propagates in a direction shifted from the direction of one light beam by 90°, and is reflected at 90° by the total reflection mirror 206 to propagate toward the total reflection mirror 211. The linearly polarized light which has reached the total reflection mirror 211 is reflected at 90° again to be superposed on the linearly polarized light beam, which has propagated straight, by a half mirror 212.

Reference numeral 208 denotes a photomask; 209, a portion of the photomask which consists of only a substrate portion exhibiting a high degree of transparency with respect to exposure light; and 210, an arbitrary pattern portion on the photomask 208. In general, in inspecting a photomask, the transmittance and phase change amount of the arbitrary pattern portion 210 with reference to the portion 209 consisting of only the substrate portion exhibiting high transparency with respect to exposure light are required. In this embodiment, a polarized state measuring unit 213 is used to observe or measure the polarized state of elliptical light produced when linearly polarized light passing through the portion 209 consisting of only the substrate portion exhibiting a high degree of transparency with respect to exposure light is superposed on linearly polarized light propagating along an optical path outside the photomask. With this observation or measurement, the values $a_x$ and $\delta$ in equations (1) and (4) are obtained.

Subsequently, the polarized state of elliptical light produced when linearly polarized light passing through the arbitrary pattern portion 210 is superposed on linearly polarized light propagating along the optical path outside the photomask is observed or measured by the polarized state measuring unit 213, thereby obtaining the values $a_x'$ and $\delta'$ in equations (5) and (7). A phase change amount $\theta$, an amplitude transmittance t, and an energy transmittance T as target values are obtained by using equations (8), (9), and (10).

In the embodiment shown in FIG. 2, the phase change amount, amplitude transmittance, and energy transmittance of each photomask portion with reference to the portion consisting of only the substrate portion exhibiting a high degree of transparency with respect to exposure light are obtained. If, however, the values $a_x$ and $\delta$ in equations (1) and (4) are obtained in advance by measuring the polarized state of elliptical light produced when two linearly polarized light beams are superposed without setting the photomask in the optical path of the linearly polarized beam which propagates straight, the absolute values of the phase change amount, amplitude transmittance, and energy transmittance of each photomask portion are obtained.

Furthermore, in the embodiment shown in FIG. 2, measurement is performed while the photomask is arranged in the optical path of one of the two linearly polarized light beams which propagates straight. Even if, however, the photomask is arranged in the optical path of the other linearly polarized light beam which is reflected at 90° by the half mirror 212, measurement can be performed without posing any problems.

Figure 3:
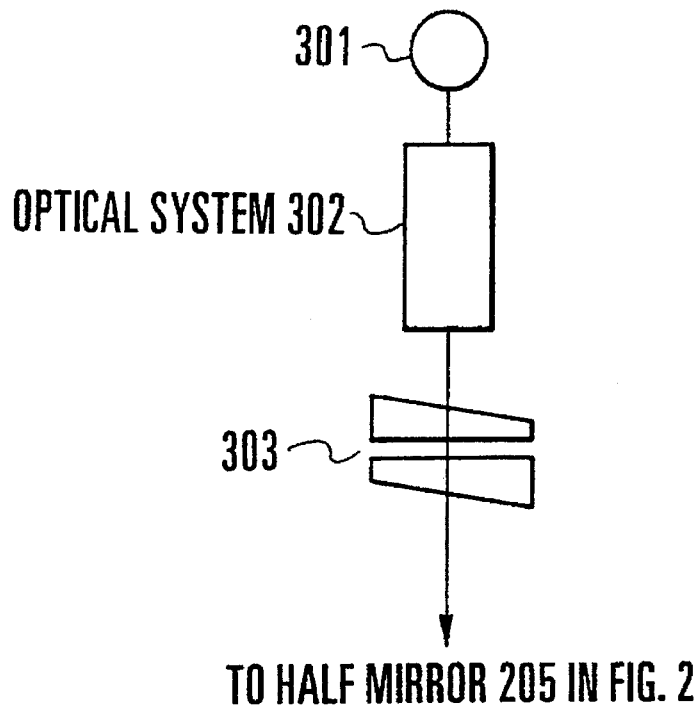
FIG. 3 is a view showing the system configuration of another embodiment of the present invention.
Figure 4:
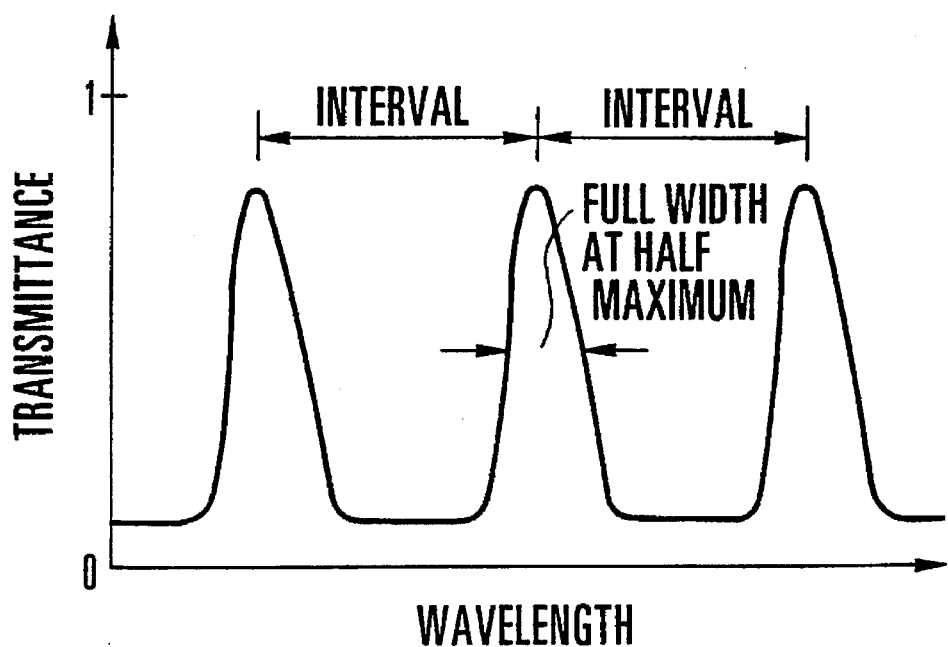
FIG. 4 is a graph showing the transmittance characteristics of an etalon used in the embodiment shown in FIG. 3.

FIG. 3 shows another embodiment of the present invention. In this embodiment, the optical path difference between the optical paths of linearly polarized light beams polarized in the orthogonal directions in the embodiment shown in FIG. 2 is set to be larger than the coherence length which can be realized by converting light emitted from a light source into monochromatic light. With this setting, a large photomask can also be inspected. In this case, the band widths of linearly polarized light beams polarized in the orthogonal directions must be reduced. For this purpose, in this embodiment, line spectra from a low-pressure mercury lamp as a light source are used. Referring to FIG. 3, reference numeral 301 denotes a light source constituted by a low-pressure mercury lamp; 302, an optical system having focusing and collimating functions; and 303, an etalon, which is known, as disclosed in, e.g., Max Born and Emil Wolf, "Principles of Optics", 6th Edition, Pergamon Press. A plurality of different light spectra are emitted from the low-pressure mercy lamp light source 301. The etalon 303 allows only a necessary line spectrum to pass therethrough. As shown in FIG. 4, the etalon 303 is a bandpass filter having a plurality of transmission band widths. Referring to FIG. 4, the central distance and full width at half maximum of the above transmission band are determined by the distance between the opposing parallel flat surfaces of the etalon and the reflectances of reflection films formed on the two flat surfaces. However, the position of the transmission band itself is determined by the angle defined by incident light beam and the parallel flat surfaces. Therefore, the setting angle of the etalon 303 is adjusted to allow transmission of only a line spectrum corresponding to i- or g-line used in a lithographic technique. The arrangement following the arrangement for extracting monochromatic light is the same as that of the embodiment shown in FIG. 2.

Assume that a laser which oscillates at a wavelength near the wavelength of exposure light is used as a light source for inspection, or an exposure light source itself is a laser and used as a light source of inspection as in excimer laser lithography. In this case, the optical systems 202 and 203 for focusing and collimating operations and the filters 203 and 303 associated with conversion to monochromatic light in the embodiments shown in FIGS. 2 and 3 can be omitted.

Figure 5:
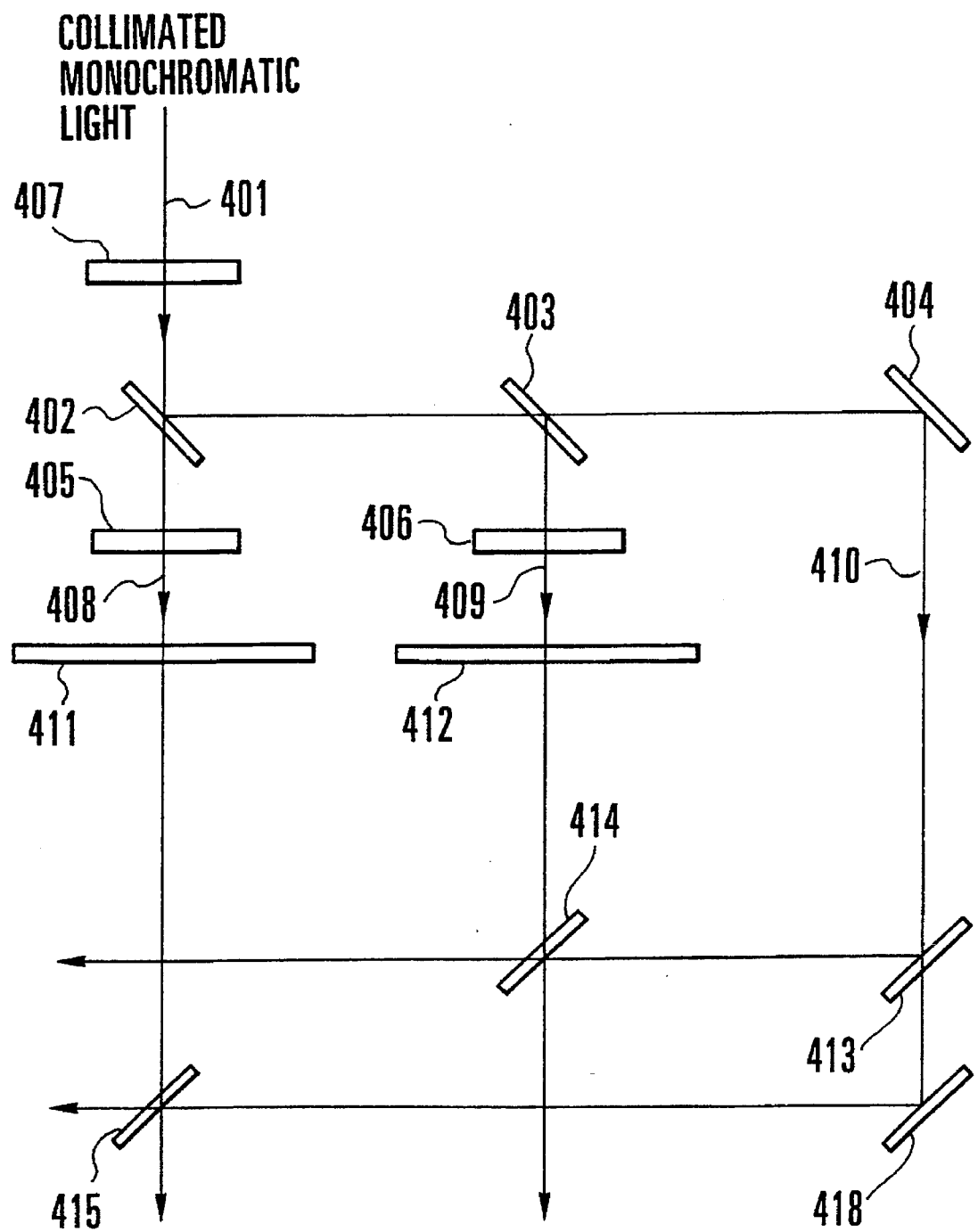
FIGS. 5 to 7 are views showing the system configurations of other embodiments of the present invention.

FIG. 5 shows still another embodiment of the present invention, in which a plurality of photomasks can be inspected at once. This embodiment exemplifies the apparatus for simultaneously inspecting two photomasks. Referring to FIG. 5, reference numeral 401 denotes collimated monochromatic light extracted by the same arrangement as that of the embodiment shown in FIG. 2 or 3; 407, a linear polarizer for converting incident light into linearly polarized light; 402, a beam splitter for allowing only a light component corresponding to ⅓ the intensity of the monochromatic light to propagate straight and reflecting light component corresponding to ⅔ the intensity at 90°; 403, a half mirror for receiving the light reflected at 90° by the beam splitter 402; 404, a total reflection mirror for receiving the light propagating straight through the half mirror 403 and totally reflecting the light at 90°; 405, a λ/2 plate for receiving the linearly polarized light propagating straight through the beam splitter 402; and 406, a λ/2 plate for receiving the linearly polarized light reflected at 90° by the half mirror 403.

The light 401 is converted into three linearly polarized light beams 408, 409, and 410, which propagate in the same direction as the original propagating direction, by the beam splitter 402, the half mirror 403, and the total reflection mirror 404. The linearly polarized light beams 408 and 409 are light beams polarized in the same direction, and the linearly polarized light beam 410 is a light beam polarized in a direction perpendicular to the linearly polarized light beam 408 or 409.

Referring to FIG. 5, reference numerals 411 and 412 denote photomasks to be inspected, which are arranged on the exit side of the λ/2 plates 405 and 406; 413, a half mirror arranged on the exit side of the total reflection mirror 404; 414, a half mirror arranged on the exit side of the photomask 409 to be inspected; 415, a half mirror arranged on the exit side of the photomask 411 to be inspected; 418, a total reflection mirror for receiving linearly polarized light propagating straight through the half mirror 413 and reflecting it at 90°; and 416 and 417, polarized state measuring units.

First of all, the polarized state of elliptical light produced upon superposition of the linearly polarized light 408 and the linearly polarized light 410, and the polarized state of elliptical light produced upon superposition of the linearly polarized light 409 and the linearly polarized light 410 are observed or measured by the polarized state measuring units 416 and 417, while the photomasks 411 and 412 are not arranged.

Subsequently, the polarized state of elliptical light produced upon superposition of the linearly polarized light 408 and the linearly polarized light 410, and the polarized state of elliptical light produced upon superposition of the linearly polarized light 409 and the linearly polarized light 410 are observed or measured by the polarized state measuring units 416 and 417, while the photomasks 411 and 412 are arranged, so that a phase change amount $\delta$, an amplitude transmittance t, and an energy transmittance T as target values are obtained by using equations (8), (9), and (10).

Figure 6:
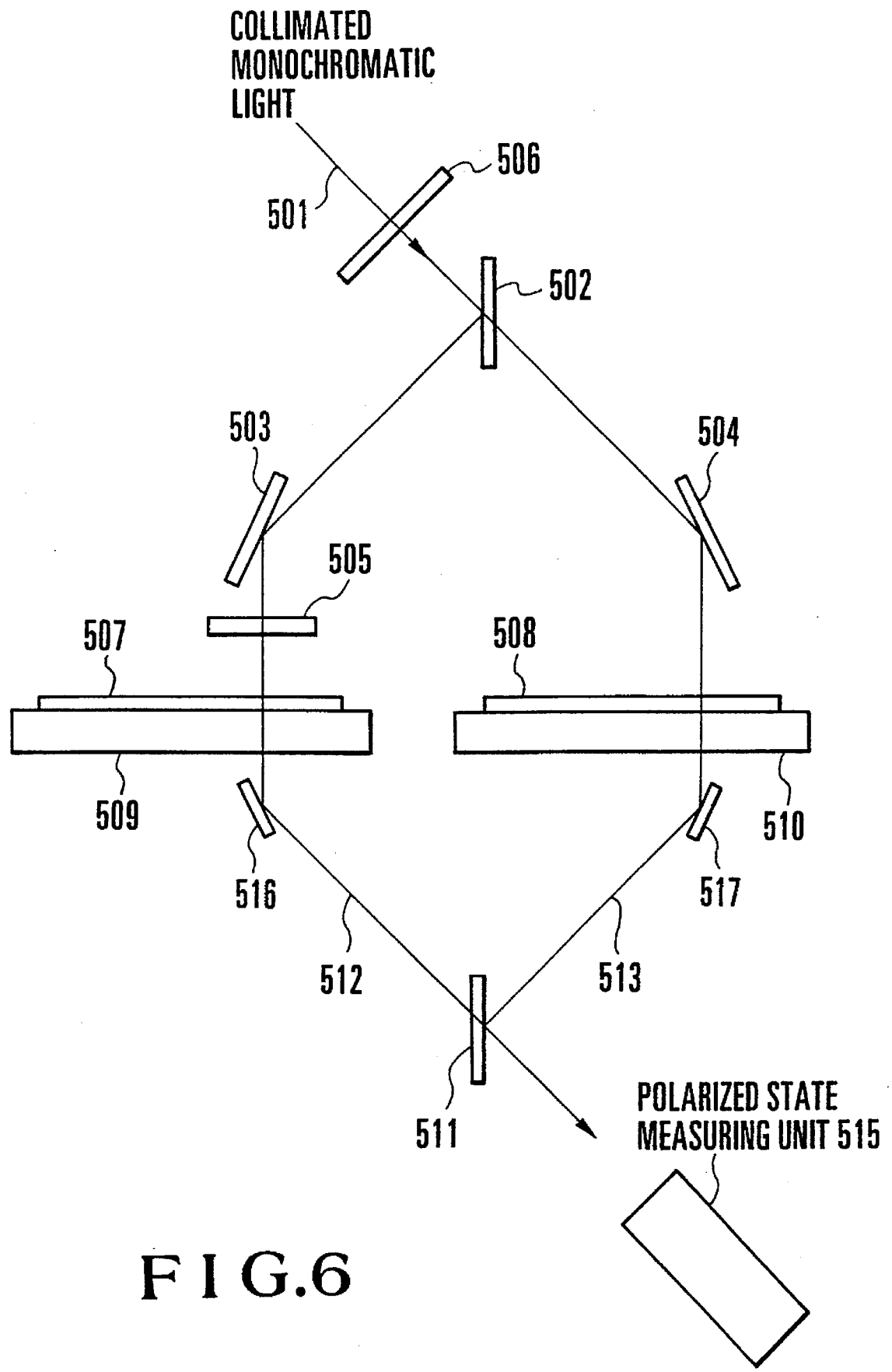

FIG. 6 shows an embodiment exemplifying the basic arrangement of an apparatus for comparing/inspecting two photomasks. Referring to FIG. 6, reference numeral 501 denotes collimated monochromatic light extracted by the same arrangement as that of the embodiment shown in FIG. 2 or 3; 506, a linear polarizer for converting the light 501 into linearly polarized light; 502, a half mirror for receiving the linearly polarized light from the linear polarizer 506; 503 and 504, total reflection mirrors for respectively receiving linearly polarized light beams split by the half mirror 502 and totally reflecting them; 505, a λ/2 plate for receiving the linearly polarized light totally reflected by the total reflection mirror 503; 507 and 508, photomasks to be inspected; 509 and 510, support tables for the photomasks 507 and 508, which tables are transparent with respect to linearly polarized light, made of the same material, and having the same thickness; 516 and 517, total reflection mirrors respectively arranged on the exit side of the photomasks 507 and 508; 511, a half mirror for receiving the linearly polarized light beams totally reflected by the total reflection mirrors 516 and 517; 512 and 513, linearly polarized light beams whose oscillating directions are perpendicular to each other; and 515, a polarized state measuring unit.

First of all, portions of the photomasks 507 and 508 which are identical to each other from the point of view of optical characteristics and pattern shape are set such that the two linearly polarized light beams 512 and 513 pass through the portions. The polarized state of elliptical light produced upon superposition of the two linearly polarized light beams 512 and 513 is measured by the polarized state measuring unit 515. Thereafter, the support tables 509 and 510 are synchronously moved. If the photomasks 507 and 508 are identical to each other, the two linearly polarized light beams 512 and 513 undergo the same phase change and the same amplitude change. Therefore, no change occurs in the polarized state of the elliptical light produced upon superposition. If, however, the photomasks 507 and 508 have different portions, the polarized state of the elliptical light changes when the linearly polarized light beams 512 and 513 pass through the portions. Assume that one of the two photomasks 507 and 508 is an original photomask, and the other photomask is a duplicated photomask. In this case, if the duplication has been perfectly completed, the state of elliptical light produced upon superposition of light beams from any portions of the two photomasks exhibits the same polarized state as that initially set. If, however, a defective portion produced in a duplication process is located in the optical path, the polarized state of elliptical light produced upon superposition changes. That is, a defective portion of a duplicated photomask can be detected.

Figure 7:
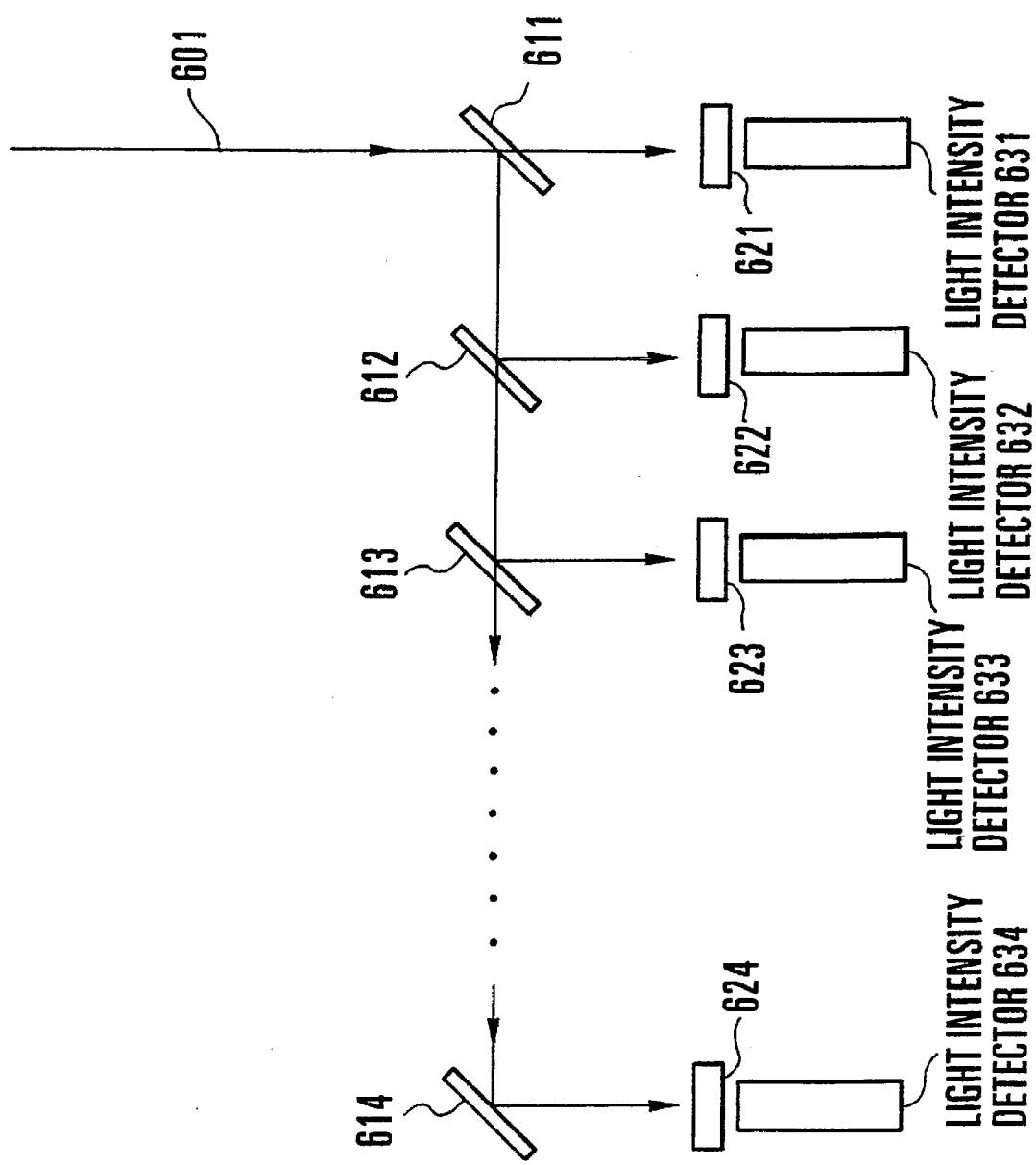

FIG. 7 shows an embodiment in which the polarized state measuring Knit in the embodiment shown in FIG. 2 is constituted by a rotating analyzer and a light intensity detector, and observation is performed by using a plurality of analyzers and detectors. In this embodiment, n detectors are used. Referring FIG. 7, reference numeral 601 denotes polarized light produced upon superposition; 631, a first light intensity detector; 632, a second light intensity detector; 633, third light intensity detector; 634, an nth light intensity detector; 621, a first analyzer; 622, a second analyzer; 623, a third analyzer; and 624, an nth analyzer. These analyzers are fixed such that their directions are shifted from each other by an angle of 360°/n. Reference numeral 611 denotes a beam splitter for allowing only a light component corresponding to 1/n the intensity of incident light to propagate straight and reflecting the remaining light components at 90°; 612, a beam splitter for reflecting only a light component corresponding to 1/(n−1) the intensity of incident light at 90° and allowing the remaining light component to propagate straight; 613, a beam splitter for reflecting only a light component corresponding to 1/(n−2) the intensity of incident light at 90° and allowing the remaining light component to propagate straight; and 614, a total reflection mirror.

With this arrangement, the polarized state of the polarized light 601 produced upon superposition can be instantly observed with a precision of 360°/n.

In the embodiments shown in FIGS. 5 to 7, a plurality of photomasks are inspected. It is, however, apparent without any special explanation that these embodiments can also be applied to inspection of a plurality of portions (to be inspected) of one photomask.

As described above, according to the embodiments of the present invention shown in FIGS. 2 to 7, the transmittance and phase change amount of each photomask portion can be easily and accurately obtained. In addition, according to these embodiments, the present invention can be applied to any objects exhibiting transparency with respect to light of a wavelength to be treated, as well as photomasks. Furthermore, if the thickness of an object is known, the refractive index and absorption coefficient or extinction coefficient of the object can be obtained from the obtained amplitude transmittance and phase change amount.

An elliptical light measuring unit used in the above embodiments will be described next.

Figure 8:
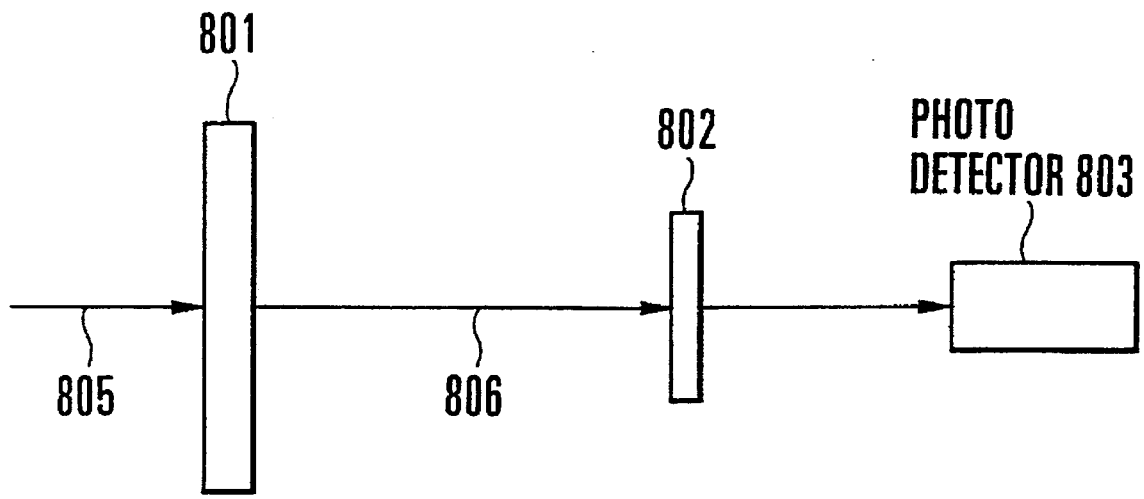
FIG. 8 is a view showing the principle of a method of measuring elliptical light.

FIG. 8 shows the basic arrangement of an elliptical light measuring unit. Referring to FIG. 8, reference numeral 801 denotes a compensator; 802, an analyzer; 803, a photodetector; 805, elliptical light to be measured; and 806, circularly polarized light produced upon conversion of the elliptical light 805 by means of the compensator 801.

Figure 9:
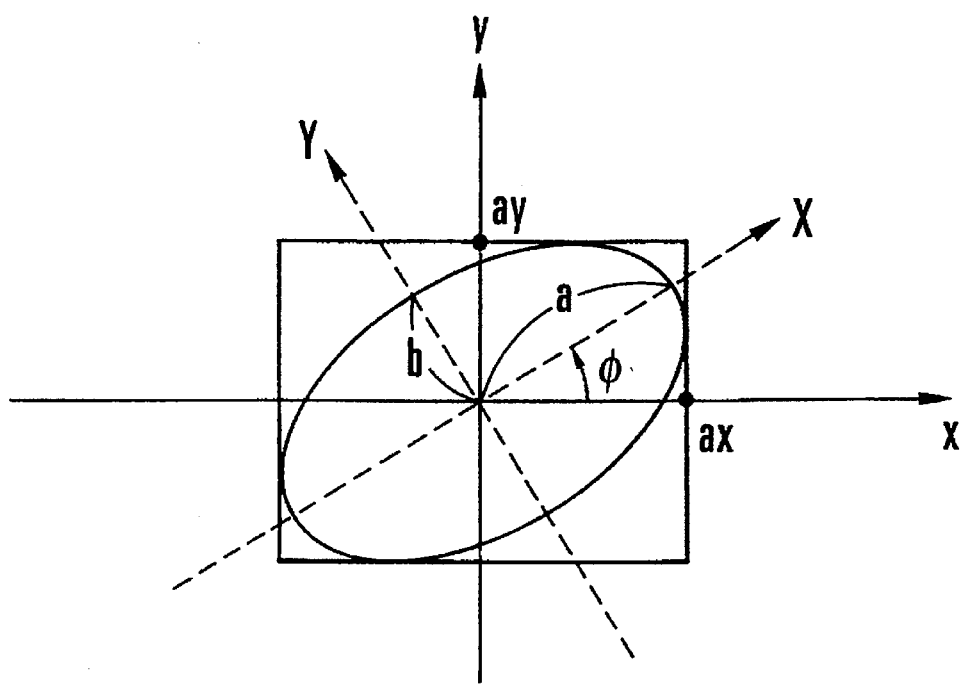
FIG. 9 is a view showing the locus of the leading end of the amplitude vector of elliptical light produced by synthesizing two linearly polarized light beams.

When the locus of the leading end of the amplitude vector of elliptical light produced upon superposition of two linearly polarized light beams expressed as equations (1) and (2) is obtained, an ellipse like the one shown in FIG. 9 is obtained. This ellipse is represented by equation (3) described above.

Figure 10:
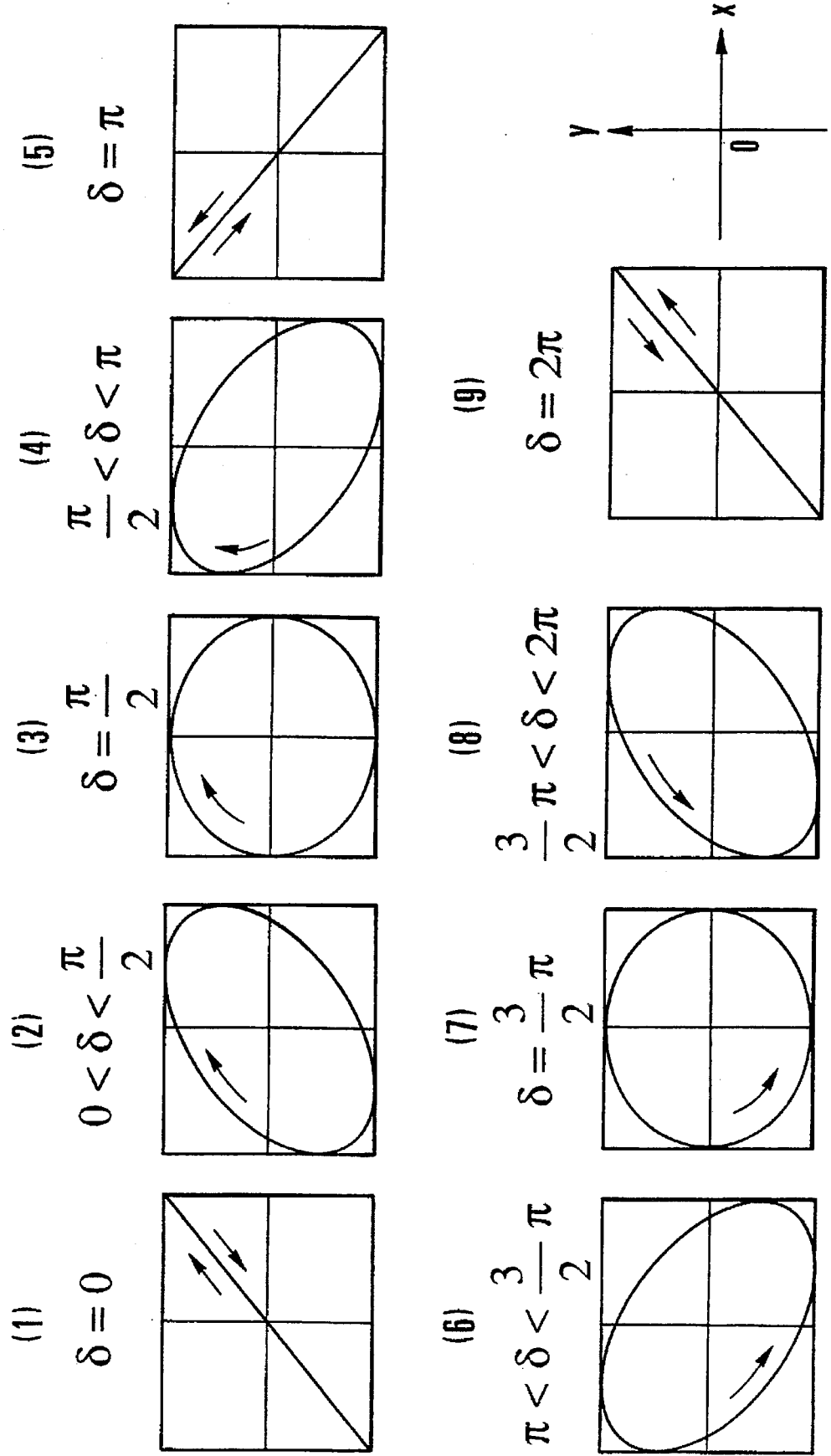
FIG. 10 is a view showing the relationship between the phase difference between two linearly polarized light beams producing elliptical light and the polarized state of the elliptical light.

FIG. 10 shows changes in the inclination of the ellipse with changes in the value of $\delta$, which are expressed according to equation (3). Referring to FIG. 10, the rotational direction of the amplitude vector is also indicated by the arrows. Referring to FIGS. 9 and 10, the direction of the long axis (apse line) of the ellipse is defined as the X-axis direction, the direction of the short axis of the ellipse is defined as the Y-axis direction, ½ the length of the long axis is defined as a, and ½ the length of the short axis is defined as b. In this case, the ellipse is given by:

$$\frac{E_x^2}{a^2} + \frac{E_y^2}{b^2} = 1 \qquad (11)$$

Letting $\phi$ be the angle defined by the x-axis and X-axis, the following relations are established between the respective variables:

$$a^2 + b^2 = a_x^2 + a_y^2 \qquad (12)$$

$$a^2 - b^2 = (a_x^2 - a_y^2)\cos 2\phi + 2a_x a_y \sin 2\phi \cos \delta \qquad (13)$$

$$ab = a_x a_y \sin \delta \qquad (14)$$

In addition, Stokes parameters $S_0$, $S_1$, $S_2$, and $S_3$ representing the polarized state and degree of polarization of the elliptical light can be expressed using the above variables a, b, and $\phi$ as follows:

$$S_0 = a_x^2 + a_y^2 = a^2 + b^2 \qquad (15)$$

$$S_1 = a_x^2 - a_y^2 = (a^2 - b^2)\cos 2\phi \qquad (16)$$

$$S_2 = 2a_x a_y \cos \delta = (a^2 - b^2)\sin 2\phi \qquad (17)$$

$$S_3 = sa_x a_y \sin \delta = 2ab \qquad (18)$$

In this case, to determine the polarized state of the elliptical light is to determine the parameters a/b and $\phi$ and the rotational direction, the parameters $a_x/a_y$ and $\phi$ and the rotational direction, or the parameters $S_1$, $S_2$, and $S_3$.

A method of determining the polarized state of elliptical light will be described next with reference to FIG. 8. Elliptical light can be split into two perpendicular linearly polarized light beams respectively represented by equations (1) and (2). In this case, the compensator 801 forcibly adjusts the phase difference between these two linearly polarized light beams to $\pi/2$ or $3\pi/2$. At the same time, the compensator 801 adjusts the value of $a_x/a_y$ to 1. The arrangement of this compensator is disclosed in detail in Max Born and Emil Wolf, "Principles of Optics", 6th Edition, Pergamon Press.

Assume that the circularly polarized light 806 is obtained by proper polarization. In this case, even if the analyzer 802 is rotated, the polarized state of the circularly polarized light 806 is not changed. Consequently, the output from the photodetector 803 remains the same. Therefore, the phase difference $\delta$ between the two linearly polarized light beams, which is represented by equation (4), can be obtained from the phase difference given by the compensator 801. In addition, the original value of $a_x/a_y$ can be known from the magnitude of the adjustment value given to adjust the value of $a_x/a_y$ to 1.

This method, however, requires the following cumbersome operations. First of all, the phase difference given by the compensator 801 and the adjustment amount of $a_x/a_y$ are set to be given values. The analyzer 802 is then rotated by a ½ rotation to check whether the output from the photodetector 803 is dependent on the angle of the analyzer 802. These operations must be repeated until the above dependence is nullified. In addition, the compensator 801 must be fixed while the analyzer 802 is rotated. For this reason, the adjustment amount given by the compensator 801 can only be set to a discrete value. These problems indicate that conversion from elliptical light into circularly polarized light is impossible, strictly speaking, unless the adjustment amount required to convert elliptical light into circularly polarized light coincides with a set value as the adjustment value given by the compensator 801. In other words, precision in determining various parameters representing the polarized state of elliptical light depends on not only measurement precision but also precision of conversion from elliptical light into circularly polarized light.

In order to solve such problems, an embodiment shown in FIGS. 11 to 14 is designed to quickly and accurately determine various parameters without converting elliptical light (to be measured) into another polarized light.

In the embodiment shown in FIGS. 11 to 14, parameters for elliptical light are determined from only four measurement values, i.e., the maximum and minimum light intensities obtained when an analyzer is rotated by a ½ rotation, the angle of the analyzer with respect to a reference direction corresponding to the maximum light intensity, and the angle of the analyzer with respect to the reference direction which corresponds to the maximum light intensity with a $\lambda/4$ plate being set in front of the analyzer. A determination method will be described in detail below with reference to FIG. 11.

Figure 11:
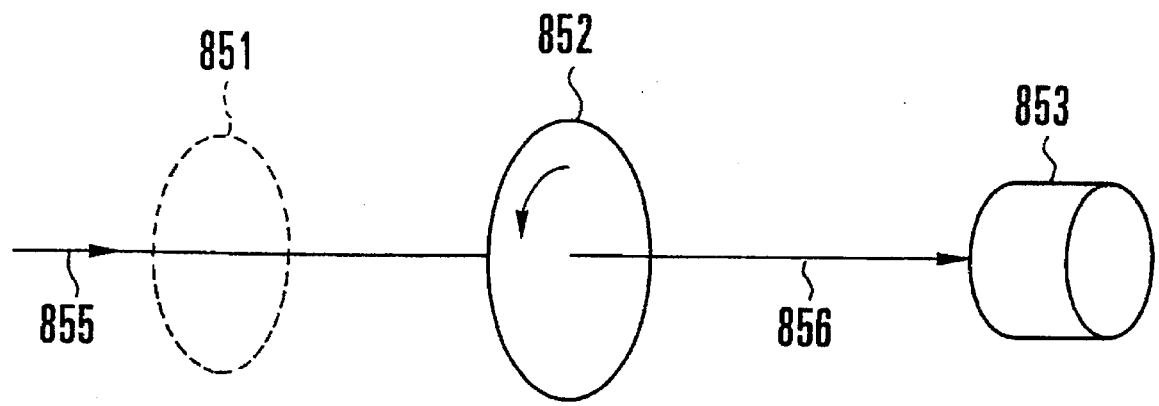
FIG. 11 is a view showing the principle of elliptical polarization in the present invention.

FIG. 11 shows the principle of a method of measuring elliptical light in the embodiment of the present invention. Referring to FIG. 11, reference numeral 851 denotes a $\lambda/4$ plate; 852, an analyzer; 853, a light intensity detector; 855, elliptical light; and 856, polarized light obtained through the analyzer 852.

The method of determining the polarized state of elliptical light by using this measurement system will be described below.

First of all, while the elliptical light 855 to be measured is incident on the analyzer 852, the analyzer 852 is rotated about the optical axis of the elliptical light in a counterclockwise direction, when viewed from the light intensity detector 853 side. With this operation, the maximum light intensity of the elliptical light 856 emerging from the analyzer 852, a rotational angle φ of the analyzer 852 when the light intensity is maximized, and the minimum light intensity of the polarized light 856 are obtained.

Subsequently, the λ/4 plate 851 is arranged on the incident side of the analyzer 852, and the analyzer 852 is rotated counterclockwise about the optical axis of the elliptical light 855 while the elliptical light 855 is sequentially caused to be incident on the λ/4 plate 851 and the analyzer 852. With this operation, the rotational angle φ of the analyzer 852 which is set when the light intensity of the elliptical light 855 emerging from the analyzer 852 is maximized is obtained.

Figure 12:
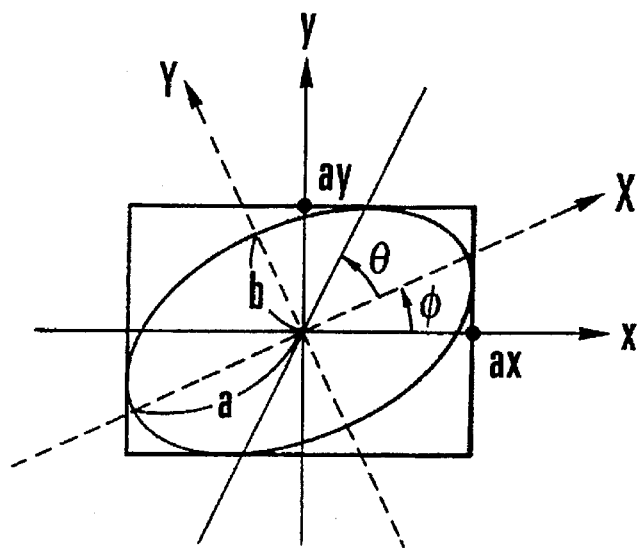
FIG. 12 is a view showing the locus of the leading end of the amplitude vector of elliptical light when viewed from the light intensity detector side in FIG. 11.

FIG. 12 shows the locus of the leading end of the amplitude vector of the elliptical light which is viewed from the light intensity detector 853 side. Referring to FIG. 12, the x-axis, the y-axis, the X-axis, the Y-axis, and values $a_x$, $a_y$, a, b, and φ are the same as those in FIG. 9, and reference symbol θ denotes the direction of the analyzer 852 measured from the X-axis. Letting (±m,±n) be the X- and Y-coordinates of intersection points between a line expressed as equation (11) and a line expressed as equation (19):

Y=Xtanθ+tm (19)

energy given by the amplitude vector in the θ direction is proportional to $(m^2+n^2)\times 2$. More specifically, $m^2$ and $n^2$ are expressed as follows:

$$m^2=a^2b^2/(b^2+a^2\tan^2\theta) \quad (20)$$

$$n^2=a^2b^2\tan^2\theta/(b^2+a^2\tan^2\theta) \quad (21)$$

In this case, a light component obtained by multiplying the amplitude vector in the (θ+α(−π/2<α<π/2)) direction by cosα passes through the analyzer 802. If, therefore, the proportional constant is represented by K, for the sake of convenience, total energy I(θ) passing through the analyzer 802 is given by:

$$I(\theta)=K\int_{-\pi/2}^{\pi/2}[a^2b^2\{1+\tan^2(\theta+\alpha)\}/\{b^2+a^2\tan^2(\theta+\alpha)\}]\cos^2\alpha\,d\alpha \quad (22)$$

If this integration is performed with θ=0 and π/2, $$I(0)=K\pi a^2b/(a+b) \quad (23)$$

$$I(\pi/2)=K\pi ab^2/(a+b) \quad (24)$$

I(0) represents the maximum value indicated by the light intensity detector; and I(π/2), the minimum value indicated by the light intensity detector.

If equations (23) and (24) are solved with respect to a and b, then $$a^2=I(0)(I(0)+I(\pi/2))/K\pi I(\pi/2) \quad (25)$$

$$b^2=I(\pi/2)(I(0)+I(\pi/2))/K\pi I(0) \quad (26)$$

Therefore, $$a/b=I(0)/I(\pi/2) \quad (27)$$

Equations (15) and (16) are then solved with respect to $a_x$ and $a_y$, and equations (25) and (26) are substituted. As a result, $$ax^2=\frac{(I(0)+I(\pi/2))\{(1+\cos 2\phi)(I(0))^2+(1-\cos 2\phi)(I(\pi/2))^2\}}{2K\pi I(0)I(\pi/2)} \quad (28)$$

ExTherefore, $$ay^2=\frac{(I(0)+I(\pi/2))\{(1-\cos 2\phi)(I(0))^2+(1+\cos 2\phi)(I(\pi/2))^2\}}{2K\pi I(0)I(\pi/2)} \quad (29)$$

$$\frac{a_x}{a_y}=\left\{\frac{(1+\cos 2\phi)(I(0))^2+(1-\cos 2\phi)(I(\pi/2))^2}{(1-\cos 2\phi)(I(0))^2+(1+\cos 2\phi)(I(\pi/2))^2}\right\}^{1/2} \quad (30)$$

With regard to δ in equation (4), according to equation (14), $$\sin^2\delta=a^2b^2/a_x^2a_y^2 \quad (31)$$

Substitutions of equations (25), (26), (28), and (29) into equation (31) yield:

$$\sin^2\delta=\frac{4(I(0))^2(I(\pi/2))^2}{\{(I(0))^2+(I(\pi/2))^2\}^2-\{(I(0))^2-(I(\pi/2))^2\}^2\cos^2 2\phi} \quad (32)$$

In this case, measurable amounts are I(0), I(π/2), and φ, and four solution candidates for δ are obtained by using equation (32). As shown in FIG. 10, since the value of φ is limited, these solution candidates can be limited to two. If φ is positive, 0< δ<π/2 or 3π/2<δ<2π. If φ is negative, π/2<δ<π or π<δ<3π/2.

In order to limit the solution candidates for δ, which have been limited to two, to one, the λ/4 plate 851 may be arranged on the incident side of the analyzer 852 to advance the phase of one of the two linearly polarized light beams in the x- and y-axis directions by π/2.

Assume the phase of the linearly polarized light beam in the y-axis direction is advanced from that of the linearly polarized light beam in the x-axis direction by π/2. In this case, δ increases by π/2 according to equations (1) to (3). At this time, φ is measured again. If φ given before insertion of the λ/4 plate 851 is positive, 0<δ<π/2 or 3π/2<δ<2π. If φ remains positive after insertion of the λ/4 plate 851, it can be determined that 3π/2<δ<2π is true. If φ becomes negative, it can be determined that 0<δ<π/2 is true.

Similarly, if π/2<δ<π or π<δ<3π/2 is true before the λ/4 plate 851 is inserted, and φ remains negative after the λ/4 plate 851 is inserted, it can be determined that π/2<δ<π. If φ becomes positive, it can be determined that π<δ<3π/2 is true.

The original value of δ, therefore, can be uniquely determined from the sign of φ before and after the λ/4 plate is inserted.

As described above, since I(0), I(π/2, and φ are the measurable amounts, all the parameters associated with the elliptical light can be determined by a determination process using equations (15) to (18), (25) to (30), and (32).

FIG. 13 shows a measurement system used to perform the method of measuring elliptical light according to the present invention. Referring to FIG. 13, reference numeral 911 denotes a light intensity detector; 921, an He—Ne laser for oscillating nonpolarized light at an output of 1 mW; 922, a polarizer arranged on the exit side of the He—Ne laser 921; 923, a half mirror arranged on the exit side of the polarizer 922; 924A and 924B, total reflection mirrors, each for reflecting a linearly polarized light beam 932, of two linearly polarized light beams 931 and 932 split by the half mirror 923, at 90°; and 925, a λ/2 plate arranged between the total reflection mirrors 924A and 924B.

Light emitted from the He—Ne laser 921 is converted into linearly polarized light by the polarizer 922 and split by the half mirror 923 into the linearly polarized light beam 931 propagating straight and the linearly polarized light beam 932 whose propagating direction is rotated through 90°. The linearly polarized light beam 932 is reflected at 90° again by the total reflection mirror 924A to propagate in a direction parallel to the linearly polarized light beam 931. The oscillating direction of the linearly polarized light beam 932 is rotated through 90° by the λ/2 plate 925 to be perpendicular to the oscillating direction of the linearly polarized light beam 931. The propagating direction of the linearly polarized light beam 932, whose linearly polarization oscillating direction is rotated through 90°, is further rotated through 90° by the total reflection mirror 924B. As a result, the linearly polarized light beam 932 is synthesized with the linearly polarized light beam 931 by the half mirror 923 to produce new polarized light 935.

This new polarized light 935 is normally elliptical light. In a special case, however, for example, in a case wherein the phase difference between the linearly polarized light beams 931 and 932 is 0 or π, the polarized light 935 becomes linearly polarized light. If the phase difference between the linearly polarized light beams 931 and 932 is π/2 or 3π/2, and the amplitude ratio between the beams is 1, the polarized light 935 becomes circularly polarized light.

FIG. 14 shows the measurement result obtained by using the measurement system shown in FIG. 13. Referring to FIG. 14, the x- and y-axes are parallel to the oscillating directions of the linearly polarized light beams 931 and 932, respectively. Assume that the angle defined by the analyzer 902 and the x-axis is θ as in the case shown in FIG. 12. In this case, measurement is performed with $0 \leq \theta \leq \pi$. With regard to $\pi < \theta < 2\pi$, a measurement value is moved symmetrical about the origin to additionally perform measurement. In this measurement, $\phi = -5°$, $I(0) = 78.55$ μW, and $I(\pi/2) = 26.6$ μW. As four candidates for δ, 77.2°, 102.8°, 257.2°, and 282.8° are obtained from these values and equation (32).

Since the value of φ is −5°, the four solution candidates are limited to the two solution candidates, i.e., 102.8° and 257.2°. A λ/4 plate 912 was inserted in front of the analyzer 902 to advance the phase of linearly polarized light in the y-axis direction by π/2. In this state, φ was checked to be negative. Therefore, δ=102.8°. That is, δ can be uniquely determined. In addition, since a/b=2.953 and $a_x/a_y=2.479$ according to equations (27) and (30), all the parameters associated with the elliptical light can be determined.

As described above, according to the embodiment shown in FIGS. 11 to 14, the maximum light intensity, the rotational angle of the analyzer which corresponds to the maximum light intensity, the minimum light intensity, and the rotational angle of the analyzer which corresponds to the maximum light intensity when the λ/4 plate is inserted are obtained, and the polarized state of the elliptical light is determined on the basis of these four values. Therefore, all the parameters required to determine the polarized state of the elliptical light can be quickly determined. In addition, since elliptical light to be measured is measured without changing it into another polarized light, all the parameters for the elliptical light can be quickly and accurately determined.

Another embodiment of the present invention, designed to measure the polarized state of elliptical light, will be described next with reference to FIGS. 15 and 16.

Figure 15:
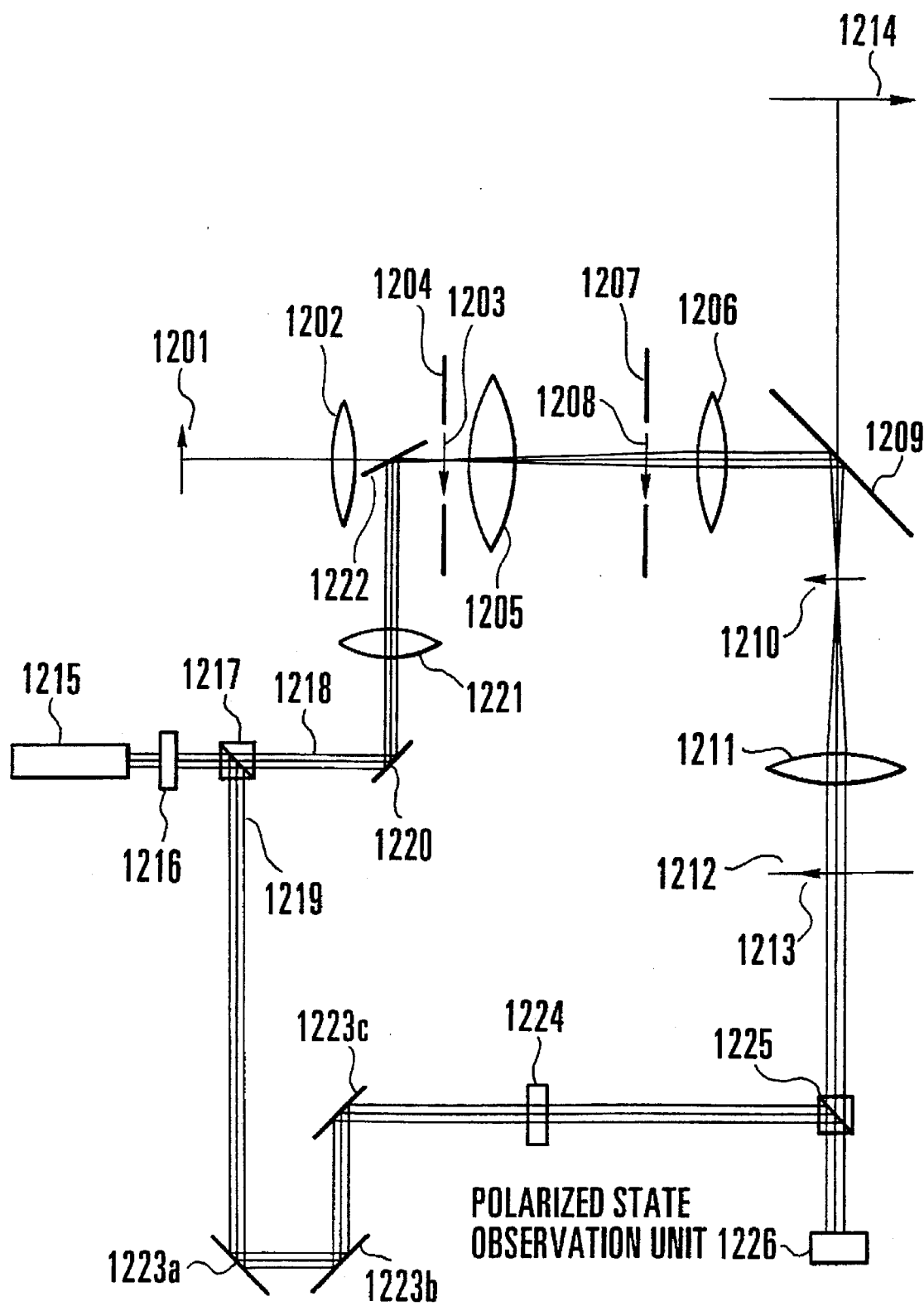
FIGS. 15, 16, and 17 are views showing embodiments of a photomask inspecting apparatus of the present invention.

In the embodiment shown in FIG. 15, reference numeral 1201 denotes a light source for observation; 1202, a condenser lens; 1203, a first real image of the light source 1201 which is formed by the condenser lens 1202; 1204, a brightness stop; 1205, a first illumination lens; 1206, a second illumination lens; 1207, a field stop; 1208, a visual field defined by the field stop 1207; 1209, a half mirror; 1210, a second real image of the light source 1201 which is formed by the first and second illumination lenses 1205 and 1206; 1211, an objective lens; and 1212, a photomask as an object to be observed. The second real image of the light source 1201 coincides with the back focal plane of the objective lens 1211. Reference numeral 1213 denotes a real image of the visual field 1208 which is formed by the second illumination lens 1206 and the objective lens 1211; and 1214, a real image of the photomask 1212.

An arrangement constituted by the components arranged between the light source 1201 and the real image 1214 serves to enlarge/observe a portion (to be inspected) of the photomask 1212. Since the arrangement is the same as that of a general microscope for metal observation, an illumination light beam and a light beam for forming the real image 1214 of the photomask are omitted. Reference numeral 1215 denotes a light source for inspection; 1216, a polarizer; and 1217, a half mirror. Light from the light source 1215 is split by the half mirror 1217 into a first linearly polarized light beam 1218 and a second linearly polarized light beam 1219. Reference numeral 1220 denotes a total reflection mirror; 1221, a lens; and 1222, a plate. The plate 1222 has a transmittance enough to transmit light from the observation light source 1201. The front focal point of the lens 1221 coincides with the center of the brightness stop 1204. Therefore, the first linearly polarized light beam 1218 is superposed and focused on the first real image 1203 of the light source for observation at the center the brightness stop 1204. Furthermore, the first linearly polarized light beam 1218 is focused at the position of the second real image 1210 of the light source for observation again. Since the position of the second real image 1210 of the light source for observation coincides with the back focal plane of the objective lens 1211, the first linearly polarized light beam 1218 passes through the objective lens 1211 to become a parallel beam, and passes through the photomask 1212. Meanwhile, the optical path of the second linearly polarized light beam 1219 is bent by mirrors 1223a to 1223c, and the light beam 1219 passes through the λ/2 plate 1224. The mirrors 1223a to 1223c serve to adjust the optical path length difference between the first linearly polarized light beam 1218 and the second linearly polarized light beam 1219 to be equal to or less than the coherence length. In addition, when the second linearly polarized light beam 1219 passes through the λ/2 plate 1224, the polarization direction of the second linearly polarized light beam 1219 becomes perpendicular to the polarization direction of the first linearly polarized light beam 1218. The first and second linearly polarized light beams 1218 and 1219 are superposed on each other by the half mirror 1225 to form elliptical light. The polarized state of the elliptical light is observed by a polarized state observation unit 1226.

In inspecting a photomask, the transmittance and phase change amount of an arbitrary portion are generally required with reference to only a portion of a substrate which exhibits high transparency with respect to exposure light. In the embodiment shown FIG. 15, the polarized state observation unit 1226 measures the polarized state of elliptical light produced when the first linearly polarized light beam 1218 passing through only a portion of a substrate which exhibits a high degree of transparency with reference to exposure light is superposed on the second linearly polarized light beam 1219. The measured values are then set to be $a_x$ and δ in equations (1) and (4).

Subsequently, the polarized state observation unit 1226 measures the polarized state of the elliptical light produced upon superposition of the first linearly polarized light beam 1218 passing through an arbitrary portion and the second linearly polarized light beam 1219. The measured values are set to be $a_x'$ and $\delta'$ in equations (5) and (7). A phase change amount, an amplitude transmittance, and an energy transmittance, which are target values, are obtained by using equations (8), (9), and (10).

In the embodiment shown in FIG. 15, the phase change amount, amplitude transmittance, and energy transmittance of each photomask portion are obtained with reference to only a portion of a substrate which exhibits a high degree of transparency with respect to exposure light are obtained. If the polarized state of elliptical light produced upon superposition of two linearly polarized light beams is measured without arranging a photomask in the optical path of the first linearly polarized light beam, i.e., without the photomask 1212, and the measured values are set to be $a_x$ and $\delta$ in equations (1) and (4), the absolute values of the phase change amount, amplitude transmittance, and energy transmittance of each photomask portion are obtained.

In the embodiment shown in FIG. 15, light emitted from the light source 1215 for inspection is parallel light. However, as such light for inspection, light from a laser oscillated at a wavelength to be inspected may be used. Alternatively, 365-nm light emitted from a lamp, e.g., a mercury lamp, may be extracted by a filter or a monochrometer to be collimated by a collimating optical system, thereby obtaining parallel light. When a very small region of the photomask 1212 is to be inspected, a relay optical system is inserted between the light source 1215 for inspection and the polarizer 1216 or between the polarizer 1216 and the half mirror 1217. With this arrangement, the sectional areas of the first and second linearly polarized light beams 1218 and 1219 may be reduced.

Figure 16:
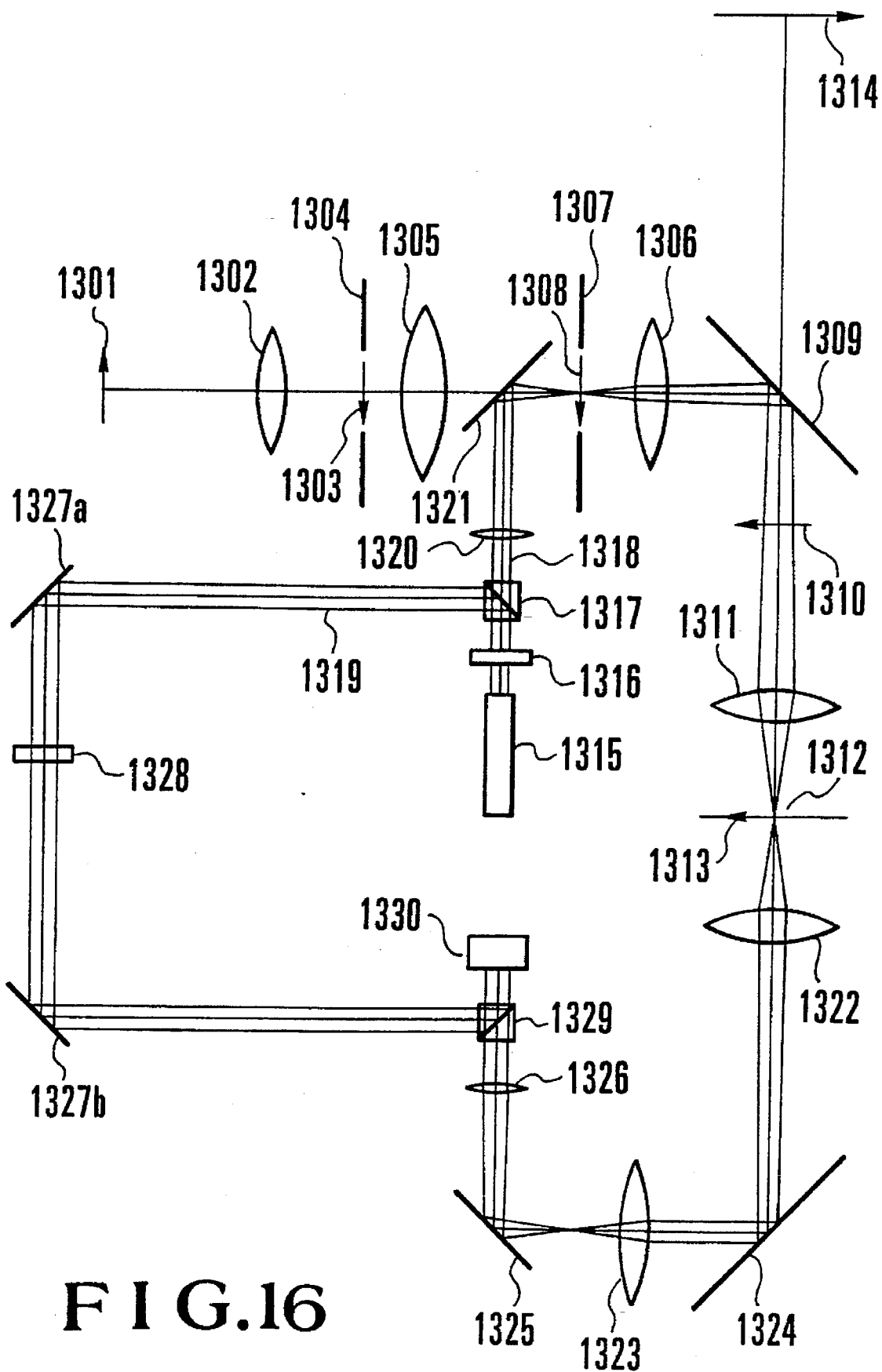

FIG. 16 shows another embodiment of the present invention which corresponds to the embodiment shown in FIG. 15. Referring to FIG. 16, reference numeral 1301 denotes a light source for observation; 1302, a condenser lens; 1303, a first real image of the light source 1301 which is formed by the condenser lens 1302; 1304, a brightness stop; 1305, a first illumination lens; 1306, a second illumination lens; 1307, a field stop; 1308, a visual field defined by the field stop 1307; 1309, a half mirror; 1310, a second real image of the light source 1301 which is produced by the first and second illumination lenses 1305 and 1306; 1311, an objective lens; and 1312, a photomask as an object to be observed. The second real image 1310 of the light source for observation coincides with the back focal plane of the objective lens 1311. Reference numeral 1313 denotes a real image of the visual field 1308 which is formed by the second illumination lens 1306 and the objective lens 1311. Reference numeral 1314 denotes a real image of the photomask 1312. An arrangement constituted by the components between the light source 1301 and the real image 1314 of the photomask 1312 serves as a unit for enlarging/observing a portion of the photomask 1312 which is to be inspected. Since the arrangement is the same as that of a general microscope for metal observation, an illumination light beam and a light beam for forming the real image 1314 of the photomask are omitted. Reference 1315 denotes a light source for inspection; 1316, a polarizer; and 1317, a half mirror. Light emitted from the light source 1315 is split by the half mirror 1317 into a first linearly polarized light beam 1318 and a second linearly polarized light beam 1319. Reference numeral 1320 denotes a lens; and 1321, a plate. The plate 1321 has a transmittance enough to transmit a sufficient amount of light emitted from the light source 1301. The front focal point of the lens 1320 coincides with the center of the visual field 1308. Therefore, the first linearly polarized light beam 1318 is focused on the center of the field stop 1307 or the visual field 1308. Since a real image of the visual field 1308 is formed at the position of the photomask 1312 by means of the second illumination lens 1306 and the objective lens 1311, the first linearly polarized light beam 1318 is focused on the photomask 1312. Consequently, a very small region of the photomask 1312 can be inspected. Reference numerals 1322, 1323, and 1326 denote first, second, and third inspection lenses; and 1324 and 1325, mirrors. The first inspection lens 1322 and the objective lens 1311 are arranged to be optically symmetrical about a plane including the photomask 1312, so are the second inspection lens 1323 and the second illumination lens 1306, the mirror 1325 and the plate 1321, and the third inspection lens 1326 and the lens 1320. With this arrangement, the first linearly polarized light beam 1318 becomes a parallel light beam after passing through the third inspection lens 1326. On the other hand, the Optical path of the second linearly polarized light beam 1319 is bent by mirrors 1327a and 1327b. Furthermore, the polarization direction of the second linearly polarized light beam 1319 is rotated through 90° by a $\lambda/2$ plate 1328. Reference numeral 1329 denotes a half mirror; and 1330, a polarized state observation unit. The mirrors 1327a and 1327b serve to adjust the optical path length difference between the first and second linearly polarized light beams 1318 and 1319 to be equal to or less than the coherence length. The first and second linearly polarized light beams 1318 and 1319 are superposed on each other by the half mirror 1329 to form elliptical light. The polarized state of this elliptical light is observed by the polarized state observation unit 1330.

The phase change amount, amplitude transmittance, and energy transmittance of each portion of the photomask 1312 are determined in the same manner as in the embodiment shown in FIG. 15.

In the embodiment shown in FIG. 16, light emitted from the light source 1315 for inspection is parallel light. However, as such light for inspection, light from a laser oscillated at a wavelength to be inspected may be used. Alternatively, 365-nm light emitted from a lamp, e.g., a mercury lamp, may be extracted by a filter or a monochrometer to be collimated by a collimating optical system, thereby obtaining parallel light.

In the embodiments shown in FIGS. 15 and 16, chromatic aberration correction corresponding to the wavelength of light from the light source for observation is performed with respect to each optical element through which only the light from the light source for observation passes; chromatic aberration correction corresponding to the wavelength of linearly polarized light is performed with respect to each optical element through which only the linearly polarized light passes; and chromatic aberration correction corresponding to the wavelengths of the light from the light source for observation and the linearly polarized light is performed with respect to each optical element through which both the light from the light source for observation and the linearly polarized light pass. Even if, however, chromatic aberration correction corresponding to the light from the light source for observation and the linearly polarized light is performed with respect to all the optical elements, no problems are posed.

As described above, according to the embodiments shown in FIGS. 15 and 16, the transmittance and phase change amount of each photomask portion can be easily and accurately obtained. In addition, the present invention can be applied not only to a photomask but also to any object exhibiting transparency with respect to light having a wavelength to be treated. Furthermore, if the thickness of an object is a known value, the refractive index and absorption coefficient or extinction coefficient of the object can be obtained from the resultant amplitude transmittance and phase change amount.

Figure 17:
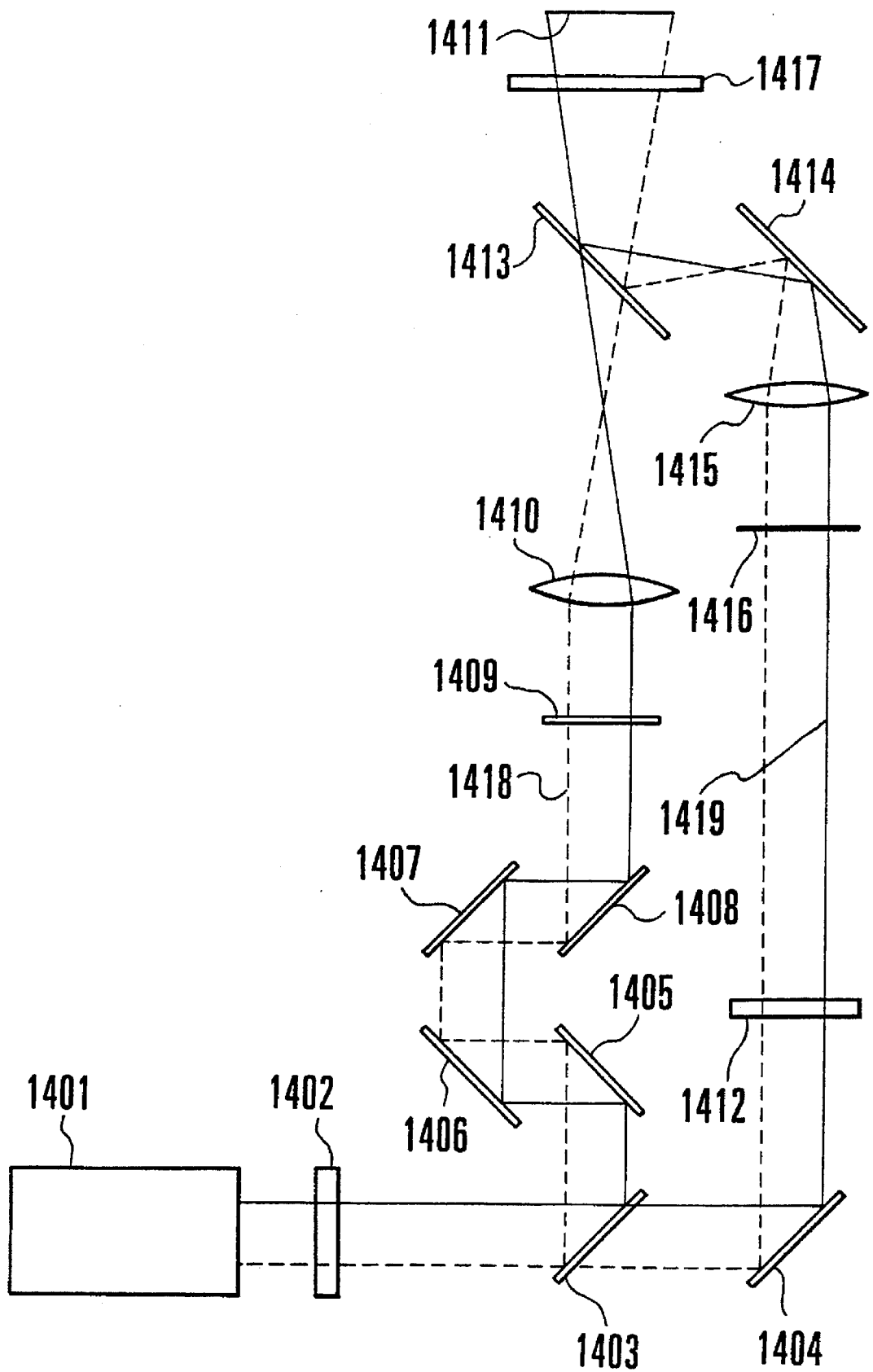

FIG. 17 shows still another embodiment of the present invention, which has a function of emphasizing a pattern of interest. Referring to FIG. 17, reference numeral 1401 denotes a light source; 1402, a polarizer for receiving light from the light source 1401 and converting it into linearly polarized light; 1403, a beam splitter, arranged on the exit side of the polarizer 1402, for splitting the linearly polarized light from the polarizer 1402 into a light beam propagating straight and a light beam reflected at 90°; 1404, a total reflection mirror for reflecting the linearly polarized light beam, propagating straight from the beam splitter 1403, at 90°; and 1405 to 1408, a group of total reflection mirrors constituting an optical path adjusting apparatus. Each of this group of total reflection mirrors reflects the linearly polarized light beam, reflected at 90° by the beam splitter 1403, by 90° to finally cause the linearly polarized light beam to emerge in the same direction as that of the linearly polarized light beam from the beam splitter 1403. Reference numeral 1409 denotes a photomask as an object to be inspected, which is arranged on the exit side of the total reflection mirrors 1405 to 1408; 1410, an objective lens arranged on the exit side of the photomask 1409; 1411, an image of the photomask 1409; 1412, a λ/2 plate arranged on the exit side of the total reflection mirror 1404; 1413, a half mirror; 1414, a total reflection mirror; 1415, an optical system equivalent in position and arrangement to the objective lens 1410 when viewed from the image 1411; 1416, an imaginary plane equivalent in position to the photomask when viewed from the image 1411; and 1417, an analyzer arranged of an optical path on the exit side of the half mirror 1413. The image 1411 is formed on the exit side of this analyzer.

As the light source 1401 used in this embodiment, a light source for providing parallel light having a wavelength required for inspection may be used. If, for example, inspection is to be performed by using the wavelength of a KrF excimer laser beam, a KrF excimer laser may be used. If inspection is to be performed by using a wavelength of 365 nm, a laser oscillating at 365 nm or a combination of a mercury lamp, a monochrometer, and a collimator may be used. Parallel light emitted from the light source 1401 is converted into linearly polarized light by the polarizer 1402 and split by the beam splitter 1403 into light beams propagating along two optical paths. One linearly polarized light beam passes through an optical path adjusting apparatus constituted by the total reflection mirrors 1405 to 1408, illuminates the photomask 1409, and forms the image 1411 through the objective lens 1410. Meanwhile, the optical path of the linearly polarized light beam propagating through the beam splitter 1403 is bent by the total reflection mirror 1404, and the polarization direction of the light beam is rotated through 90° by the λ/2 plate 1412. Thereafter, the linearly polarized light beam passes through the optical system 1415 and is superposed on the linearly polarized light beam caused to pass through the photomask by the total reflection mirror 1414 and the half mirror 1413. For the sake of descriptive convenience, one linearly polarized light beam illuminating the photomask is assumed to be an inspection linearly polarized light beam 1418; and the other linearly polarized light beam, a reference linearly polarized light beam 1419.

Letting x and y be the polarization directions of the linearly polarized light beams 1418 and 1419, and $\delta_x$ be the phase delay in the half mirror 1413, the linearly polarized light beam 1418 can be expressed as $$E_x = a_x \cos(\omega t - \delta_x)$$

Letting $\delta_y$ be the phase difference in the half mirror 1413, the linearly polarized light beam 1419 can be expressed as $$E_y = a_y \cos(\omega t - \delta_y)$$

These equations correspond to equations (1) and (2). The superposed light can be expressed as $$\frac{E_x^2}{a_x^2} + \frac{E_y^2}{a_y^2} - \frac{2E_x E_y}{a_x a_y} \cos\delta = \sin^2\delta$$

for $$\delta = \delta_x - \delta_y$$

These equations correspond to equations (3) and (4).

Let $\delta_{x1}$ be the phase delay of the inspection linearly polarized light beam 1418 in the photomask 1409, $\delta_{x2}$ be the phase delay caused when the light beam passes through a target portion (to be inspected) of the photomask, and $\delta_{x3}$ be the phase delay of the optical path extending to the image surface after passing through the photomask 1409, provided that the beam splitter 1403 is considered to be a start point. In addition, let $\delta_{y1}$ be the phase delay of the reference linearly polarized light beam 1419 on the imaginary plane 1416, and $\delta_{y3}$ be the phase delay of the optical path extending from the imaginary plane 1416 to the image surface. In this case, the above equation corresponding to equation (4) becomes $$\delta = (\delta_{x1} + \delta_{x2} + \delta_{x3}) - (\delta_{y1} + \delta_{y3}) \tag{33}$$

In this case, $\delta_{x3}$ is a function of the position of the inspection linearly polarized light beam on the photomask but is constant with respect to diffracted light emerging from a given point of the photomask and coincides with $\delta_{y3}$ of the reference linearly polarized light beam passing through a corresponding point of the imaginary plane 1416. Therefore, equation (33) is rewritten into $$\delta = (\delta_{x1} + \delta_{x2}) - \delta_{y1} \tag{34}$$

Figure 18:
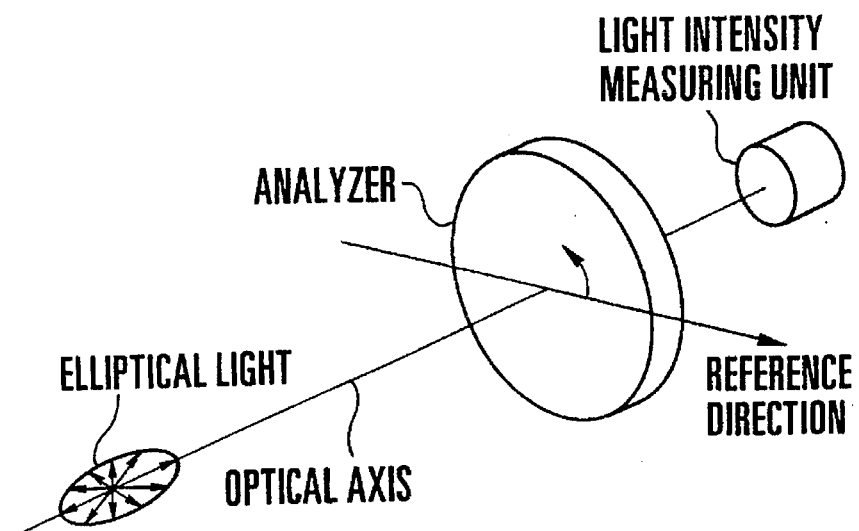
FIG. 18 is a view showing a method of calculating δ and $a_x$ in the embodiment shown in FIG. 17.

In the embodiment shown in FIG. 17, a two-dimensional CCD camera is arranged at the image 1411. While the analyzer 1417 is rotated, the output intensity of a CCD element for receiving an image of one point (of interest) of the photomask is monitored, and $\delta$ in equation (34) and $a_x$ in equation (1) are obtained by the method disclosed in Wolfgang Budde, "Photoelectric Analysis of Polarized Light", APPLIED OPTICS, No. 3, Vol. 1, May 1962. More specifically, as shown in FIG. 18, the analyzer 1417 set to be perpendicular to the optical axis is rotated about the optical axis by a 1/n rotation x n times=1 rotation (n is an integer), and an output from the light intensity detector at each inclination of the analyzer is read. Letting $I_i$ be the output from the light intensity detector when the direction of the analyzer, set at the first rotation (i=1, 2, 3, . . . ) of the analyzer, is given by (360°/n) x i=$\alpha_i$ (n is an integer) with respect to a reference direction assumed within a plane perpendicular to the optical axis, $k_0$, $k_1$, and $k_3$ expressed as the following equations are obtained:

$$k_0 = \sum_{ni=1}^{ln} I_i \quad (35)$$

$$k_1 = - \sum_{ni=1}^{ln} I_i \cos 2\alpha i \quad (36)$$

$$k_2 = - \sum_{ni=1}^{ln} I_i \sin 2\alpha i \quad (37)$$

As a result, $\delta$ and $a_x$ can be expressed as $$\delta = \cos^{-1}\left(\frac{k_2}{\sqrt{k_0 - k_1}}\right) \quad (38)$$

$$a_x = \sqrt{k_0 - k_1} \quad (39)$$

Subsequently, $\delta$ and $a_x$ are obtained following the same procedures as those described above without the photomask 1409. As is apparent from equation (34), the difference between the two values $\delta$ is the phase delay caused when the linearly polarized light beam passes through the photomask, and the ratio between the two values $a_x$ is the amplitude transmittance. An energy transmittance is obtained by squaring this ratio.

In addition, as is apparent from equations (3) and (34), since the polarized state of elliptical light is determined in accordance with the optical characteristics of a pattern, if the direction of the long axis of elliptical light produced at an image portion of a special pattern, e.g., a pattern designed to only give a phase shift, is caused to coincide with the direction of the analyzer 1417, an image is obtained with the special pattern being emphasized.

Assume that the optical path adjusting apparatus constituted by the total reflection mirrors 1405 to 1408 is driven by a high-precision displacing unit using a piezoelectric element (not shown) with respect to a special pattern, e.g., a pattern designed to only give a phase shift, and $\delta_{x1}$ in equation (34) is adjusted to set $\delta$ to be $n\pi$ (n is an integer). In this case, polarized light produced upon superposition at an image portion of the specific pattern becomes linearly polarized light. Therefore, when the direction of the linearly polarized light produced upon superposition is caused to coincide with the direction of the analyzer 1417, a further emphasized image of the specific pattern can be obtained.

If the photomask 1409 is constituted by a light-shielding member, a substrate, and an object for delaying the phase of light with respect to light passing through a substrate portion, $\delta_{x1}$ in equation (34) is adjusted with respect to the substrate portion to set $\delta$ to be $n\pi$ (n is an integer). With this operation, polarized light passing through an image on the substrate portion becomes linearly polarized light. When the analyzer 1417 is set in a direction perpendicular to the direction of the linearly polarized light, an image of only the object for delaying the phase of light with respect to light passing through the substrate portion can be obtained.

Figure 19:
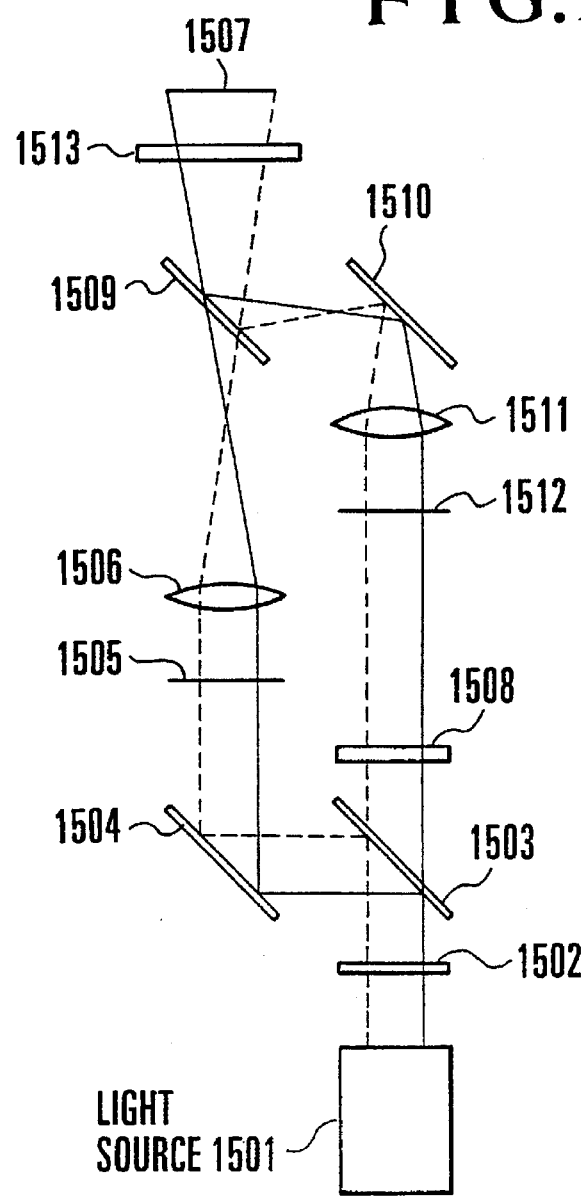
FIG. 19 is a view showing still another embodiment of the photomask inspecting apparatus of the present invention.

FIG. 19 shows still another embodiment of the present invention. Referring to FIG. 19, reference numeral 1501 denotes a light source; 1502, a polarizer arranged on the exit side of the light source; 1503, a beam splitter arranged on the exit side of the polarizer 1502; 1504, a total reflection mirror for reflecting, at 90°, a linearly polarized light beam which is split from light from the polarizer 1502 by the beam splitter 1503 and reflected at 90° thereby; 1505, a photomask as an object to be inspected which is arranged on the exit side of the total reflection mirror 1504; 1506, an objective lens arranged on the exit side of the photomask 1505; 1507, an image of the photomask 1505; 1508, a $\lambda/2$ plate for receiving a linearly polarized light beam propagating straight through the beam splitter 1503; 1509, a half mirror; 1510, a total reflection mirror; 1511, an optical system equivalent in position and arrangement to the objective lens 1506 when viewed from the image 1507; 1512, an imaginary plane equivalent in position to the photomask when viewed from the image 1507; and 1513, an analyzer. As the light source 1501, a light source for providing parallel light having a wavelength required for inspection may be used. If, for example, inspection is to be performed by using the wavelength of a KrF excimer laser beam, a KrF excimer laser may be used. If inspection is to be performed by using a wavelength of 365 nm, a laser oscillating at 365 nm or a combination of a mercury lamp, a monochrometer, and a collimator may be used.

Referring to FIG. 19, parallel light emitted from the light source 1501 is converted into linearly polarized light by the polarizer 1502 and split into linearly polarized light beams propagating along two optical paths by the beam splitter 1503. One linearly polarized light beam illuminates the photomask 1505 and forms the image 1507 via the objective lens 1506. The polarization direction of linearly polarized light beam propagating straight through the beam splitter 1503 is rotated through 90° by the $\lambda/2$ plate 1508. Thereafter, the linearly polarized light beam passes through the optical system 1511 to be superposed on the linearly polarized light beam passing through the photomask 1505 by the total reflection mirror 1510 and the half mirror 1509. In the embodiment shown in FIG. 19, a two-dimensional CCD camera is set at the position of the image 1507 to be used as an image observing means. Although the operation principle of this embodiment is the same as that of the embodiment shown in FIG. 17, polarized light produced upon superposition at an image portion corresponding a specific pattern cannot be generally converted into linearly polarized light. The embodiment shown in FIG. 19, however, is designed to omit the optical path adjusting apparatus in the embodiment shown in FIG. 17. For this reason, in this embodiment, there is no optical path difference between linearly polarized light beams passing through two optical paths and oscillating in directions perpendicular to each other, disregarding a phase change caused when the linearly polarized light beams pass through the photomask 1505. Therefore, limitations imposed on the coherence length of light emitted from the light source 1501 are very moderate.

In the embodiments shown in FIGS. 17 and 19, if the wavelength of light used for inspection is closer to the ultraviolet region than to the visible region, members, each constituted by a plate having a thin metal film, as of chromium or aluminum, deposited thereon and having at least an exit surface subjected to antireflection treatment, are used as the beam splitters 1403 and 1503 and the half mirrors 1413 and 1509. Chromatic aberration correction is performed with respect to each optical element through which linearly polarized light passes, in accordance with the wavelength of the linearly polarized light.

As described above, according to the embodiments of the present invention shown in FIGS. 17 to 19, the transmittance and phase change amount of each photomask portion can be easily and accurately obtained. In addition, since only a specific pattern can be imaged, or an image having the specific pattern emphasized can be formed, the shape of the specific pattern can be inspected. The present invention can be generally applied to objects exhibiting transparency with respect to light having a wavelength to be treated, as well as a photomask. Furthermore, if the thickness of an object is a known value, the refractive index and absorption coefficient or extinction coefficient of the object can be obtained from obtained amplitude transmittance and phase change amount.

In an optical instrument such as the present invention, an optical path must sometimes be adjusted. In this case, an inexpensive device is required, which imposes no limitations on a light beam propagating along an optical path to be adjusted.

Figure 20:
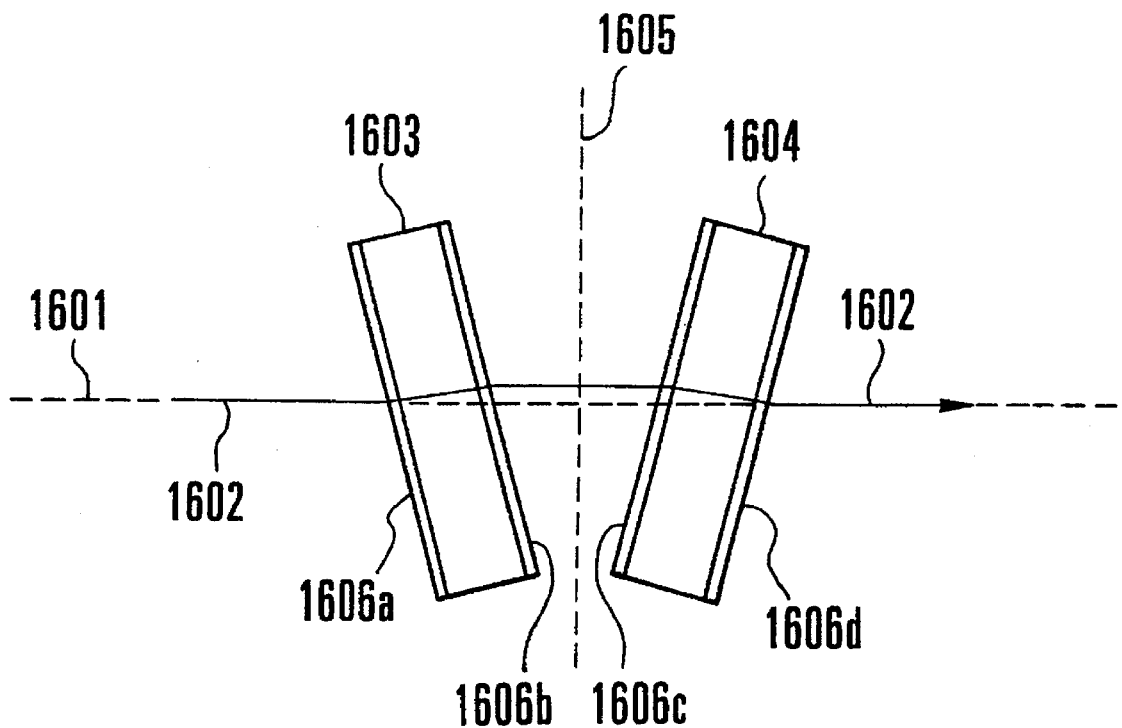

FIG. 20 shows an embodiment suitable for solving such a problem. This embodiment is basically designed such that two plates are arranged to be symmetrical about a plane perpendicular to an optical path to be adjusted. The embodiment of the present invention will be described below with reference to the accompanying drawings. Referring to FIG. 20, reference numeral 1601 denotes an optical axis; 1602, a light beam propagating along the optical axis 1601; 1603 and 1604, plates, each made of an optically isotropic material exhibiting transparency or a high degree of transparency with respect to the wavelength of the light beam 1602; 1605, a plane perpendicular to the optical axis 1601; and 1606a to 1606d, dielectric multi layers. The plates 1603 and 1604 are arranged to be symmetrical about the plane 1605 perpendicular to the optical axis. With this arrangement, although the light beam 1602 deviates from the optical axis upon passing through one plate 1603, the light beam 1602 propagates along the original optical axis upon passing through the other plate 1604. That is, no deviation from the optical axis occurs. In addition, since each of the plates 1603 and 1604 is made of an optically isotropic material, the light beam 1602 need not be a linearly polarized light beam. The optical path can be adjusted by adjusting the angles defined by the plates 1603 and 1604 and the plane 1605 or the optical axis 1601 while maintaining the symmetry of the plates 1603 and 1604 with respect to the plane 1605. Surface reflected light as noise to be removed from an optical unit is prevented by the dielectric multi layers 1606a to 1606d.

FIG. 21 shows an arrangement designed to facilitate a check on the optical axis when the optical path is actually adjusted by using the optical path adjusting apparatus shown in FIG. 20. The same reference numerals in FIG. 21 denote the same parts as in FIG. 20. Reference numeral 1655, a slide glass plate having a scattering flat surface; 1656, a mark such as a graphic pattern formed on a surface of the slide glass plate 1655; 1657, a drawing rod; 1658a and 1658b, fixed pieces fixed to the drawing rod 1657; and 1659a and 1659b, fixing pins.

An optical axis position checking operation as an important function of the embodiment shown in FIG. 21 will be described next. First of all, the drawing rod 1657 is pushed until the fixed piece 1658a is brought into contact with the fixing pin 1659a. As a result, the slide glass plate 1655 is located in the optical path. The position of the light beam 1602 on the slide glass plate 1655 is checked by using the mark 1656 in the absence of the two plates 1603 and 1604.

Subsequently, the plates 1603 and 1604 are set such that the angles defined by the plates 1603 and 1604 and the optical axis 1601 are adjusted to obtain a predetermined optical path. In this case, as described in the embodiment shown in FIG. 20, if the plates 1603 and 1604 are not symmetrical about the plane perpendicular to the optical axis 1601, the position of the light beam 1602 on the slide glass plate 1655 is displaced from the initial position. If no such a displacement occurs, it indicates that the plates 1603 and 1604 are properly set. After the position of the optical axis is checked, the drawing rod 1657 is withdrawn until the fixed piece 1658b is brought into contact with the fixing pin 1659b. The slide glass plate 1655 coupled to the drawing rod 1657 is moved outside the optical path and hence does not interfere with the propagation of the light beam 1602. In the embodiment shown in FIG. 21, the slide glass plate 1655 is used as an optical axis position checking plate in an optical axis position detecting means. However, a paper plate, a metal plate, or the like which has recesses/projections on its surface, or an object for emitting scattering light may be used. If the wavelength of the light beam 1602 is outside the ultraviolet region, a paper plate containing a material for emitting fluorescent light, e.g., a fluorescent dye, or a metal plate coated with a fluorescent material, e.g., ethylsalicylate, may be used.

FIG. 22 shows a modification of the embodiment shown in FIG. 20. The same reference numerals in FIG. 22 denote the same parts as in FIG. 20. An important function of this modification is to electrically perform an optical axis position checking operation. First of all, a two dimensional position sensor 1665 is located in the optical path by using a mechanism (not shown). The position of a light beam 1602 on the two-dimensional position sensor 1665 is checked by using a control circuit 1666 in the absence of two plates 1603 and 1604. The plates 1603 and 1604 are then set such that the angles defined by the plates 1603 and 1604 and an optical axis 1601 are adjusted to obtain a predetermined optical path. In this case, as described in the embodiment shown in FIG. 20, if the plates 1603 and 1604 are not symmetrical about the plane perpendicular to the optical axis 1601, the position of the light beam 1602 on the two-dimensional position sensor 1665 is displaced from the initial position. If no such a displacement occurs, it indicates that the plates 1603 and 1604 are properly set. If the two-dimensional position sensor 1665 is moved outside the optical path by using a mechanism (not shown) after the optical axis position is checked, the two-dimensional position sensor 1665 does not interfere with the propagation of the light beam 1602. Although the embodiment shown in FIG. 22 uses the two-dimensional position sensor 1665, any device capable of electrically detecting the spot position of light, such as a two-dimensional CCD device, may be used.

Each plate in the embodiments shown in FIGS. 20 to 22 has a dielectric multi layer formed on its surface to prevent surface reflection. However, a dielectric single layer may be formed instead of the dielectric multi layer.

As described above, in each of the optical path adjusting apparatuses in the embodiments shown in FIGS. 20 to 22, two plates made of an optically isotropic material exhibiting transparency or a high degree of transparency With respect to the wavelength of incident light are set to be symmetrical about the plane perpendicular to the optical axis of the incident light. With this arrangement, no deviation from the optical axis occurs. In addition, since each plate is made of an optically isotropic material, a light beam propagating along the optical axis need not be a linearly polarized light beam. Furthermore, each unit has a simple arrangement and can be obtained at low material and process costs. Moreover, each unit allows a check on the position of an optical axis without interfering with the propagation of a light beam. Since a surface of each plate is subjected to antireflection treatment, no noise is generated.

Figure 23:
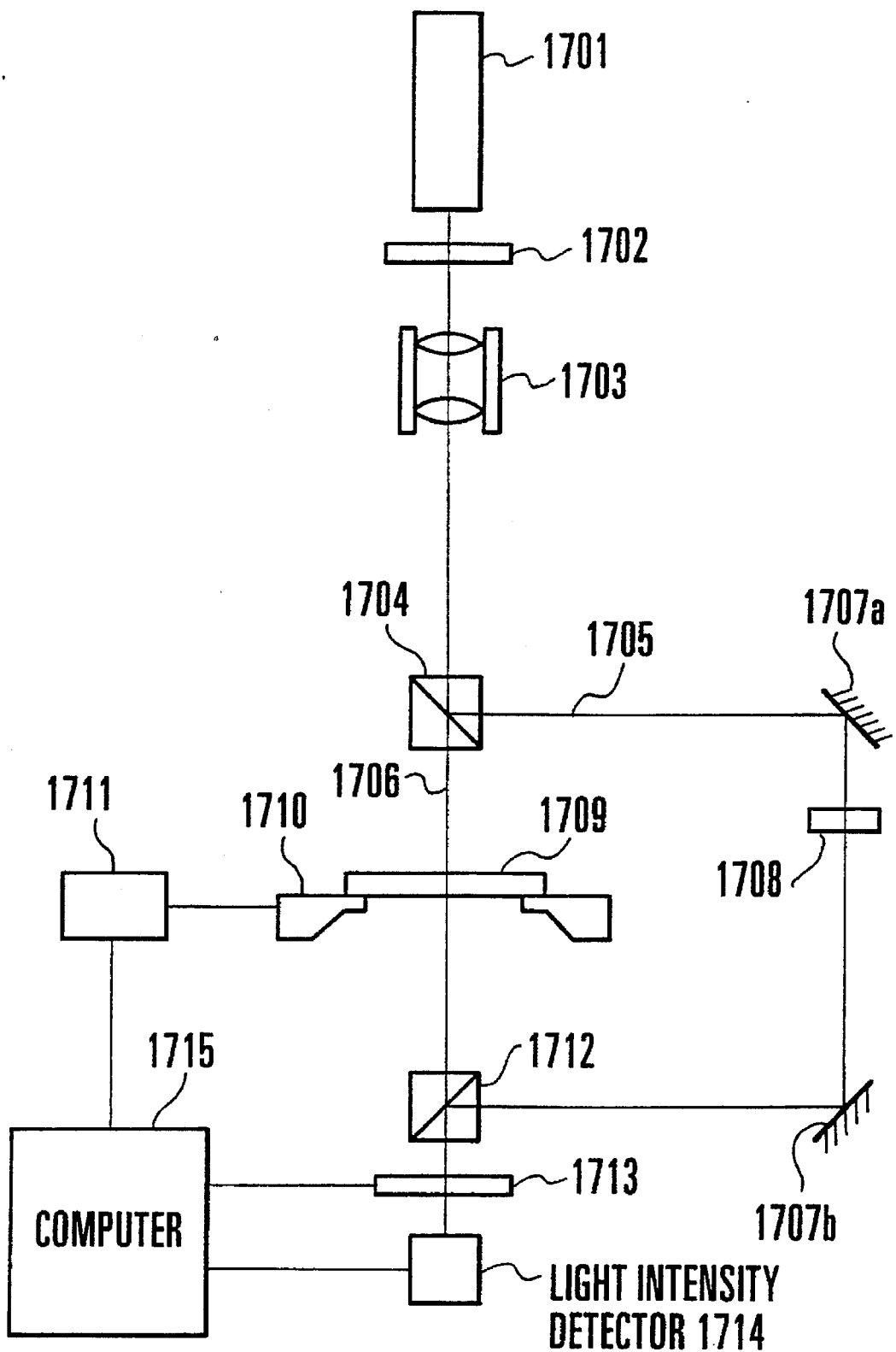
FIGS. 23, 24, and 25 are views showing other embodiments of the photomask inspecting apparatus of the present invention.

FIG. 23 shows still another embodiment of the present invention. Reference numeral 1701 denotes a laser for emitting nonpolarized light; 1702, a polarizer arranged on the exit side of this laser 1701; 1703, a reduction optical system arranged on the exit side of the polarizer 1702; and 1704, a beam splitter arranged on the exit side of the reduction optical system 1703. A laser beam emitted from the laser 1701 is converted into linearly polarized light by the polarizer 1702. The cross-sectional area of linearly polarized light is reduced by the reduction optical system 1703 and split into beams propagating along two optical paths by the beam splitter 1704. Reference numerals 1705 and 1706 denote split beams; 1707a and 1707b, total reflection mirrors arranged on one of the optical paths split by the beam splitter 1704; and 1708, a λ/2 plate arranged between the total reflection mirrors 1707a and 1707b. The polarized plane of the beam 1705 is rotated in a direction perpendicular to the beam 1706 by the λ/2 plate 1708. Reference numeral 1709 denotes a photomask to be inspected; 1710, a stage for supporting the photomask to be inspected; and 1711, a driving circuit for the stage 1710. The photomask 1709 is moved within a plane perpendicular to the beam 1706 by the stage 1710 and the driving circuit 1711 therefor. Reference numeral 1712 denotes a half mirror arranged on the exit side of the photomask 1709 to superpose the beams 1705 and 1706 on each other; 1713, a rotatable analyzer arranged on the exit side of the half mirror 1712; 1714, a light intensity detector arranged on the exit side of the analyzer 1713; and 1715, a control computer for controlling the operations of the driving circuit 1711, the analyzer 1713, and the light intensity detector 1714. Assume that the polarization direction of the beam 1706 is the x direction, and the polarization direction of the beam 1705 passing through the λ/2 plate 1708 is the y direction. In this case, letting $\delta_x$ be the phase delay at the half mirror 1712, the beam 1706 can be expressed as $$E_x = a_x \cos(\omega t - \delta_x)$$

Letting $\delta_y$ be the phase delay at the half mirror 1712, the beam 1705 can be expressed as $$E_y = a_y \cos(\omega t - \delta_y)$$

These equations correspond to equations (1) and (2). Light produced upon superposition is then expressed as $$\frac{E_x^2}{a_x^2} + \frac{E_y^2}{a_y^2} - \frac{2E_x E_y}{a_x a_y} \cos\delta = \sin^2\delta$$

This equation corresponds to equation (3). In this case, $$\delta = \delta_x - \delta_y$$

This equation corresponds to equation (4). The values of $a_x$, $a_y$, and $\delta$ in equation (3) can be determined by using the analyzer 1713 and the light intensity detector 1714.

When the values of $\delta$ and $a_x$ obtained while the photomask 1709 is not set on the stage 1710 are represented by $\delta''$ and $a_x''$, respectively, a phase change amount $\theta$ produced when the beam 1706 passes through the photomask 1709, and an energy transmittance T are given by $$\theta = \delta - \delta'' \tag{40}$$

$$T = (a_x/a_x'')^2 \tag{41}$$

Therefore, $\delta''$ and $a_x''$ are obtained first before the photomask 1709 is set on the stage 1710, and the photomask 1709 is then set on the stage 1710. The control computer 1715 issues a command to the driving circuit 1711 to control the stage 1710 so as to superpose a measurement start portion of the photomask 1709 on the beam 1706, and stops the stage 1710 at the corresponding position. Thereafter, $\delta$ and $a_x$ are obtained, and $\delta$ and T are calculated according to equations (40) and (41). Subsequently, the control computer 1715 issues a command to the driving circuit 1711 to control the stage 1710 so as to superpose the next measurement portion of the photomask 1709 on the beam 1706, and stops the stage 1710 at the corresponding position. Thereafter, $\delta$ and $a_x$ are obtained, and $\theta$ and T are calculated according to equations (40) and (41). By repeating the above procedures, the transmittance distribution and phase change amount distribution of the photomask 1709 are obtained. Defects and the like caused by factors in the manufacturing of the photomask 1709 can be known by comparing the design transmittance distribution and design phase change amount distribution of the photomask 1709 with the distributions actually obtained in the present invention. Assume that a predetermined range is set with respect to transmittances or phase change amounts, and only a portion exhibiting a measurement value falling within the range is displayed. In this case, only a pattern of a phase or transmittance of interest can be imaged.

Figure 24:
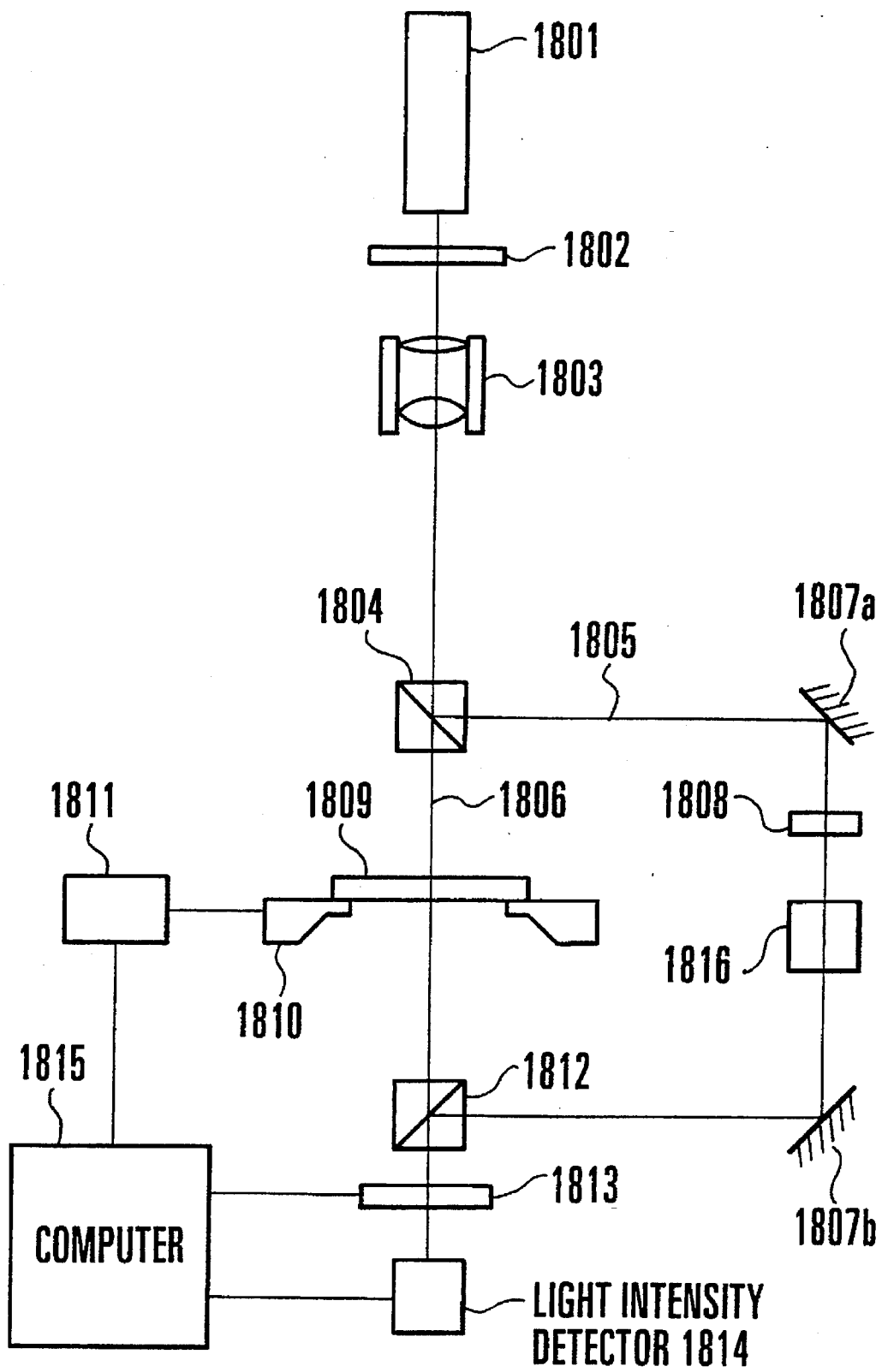

FIG. 24 shows a modification of the embodiment shown in FIG. 23. Referring to FIG. 24, reference numeral 1801 denotes a laser for emitting nonpolarized light; 1802, a polarizer; 1803, a reduction optical system; and 1804, a beam splitter. A laser beam emitted from the laser 1801 is converted into linearly polarized light by the polarizer 1802. The cross-sectional area of linearly polarized light is reduced by the reduction optical system 1803 and split into beams propagating along two optical paths by the beam splitter 1804. Reference numerals 1805 and 1806 denote split beams; 1807a and 1807b, total reflection mirrors; and 1808, a λ/2 plate. The polarized plane of the beam 1805 is rotated in a direction perpendicular to the beam 1806 by the λ/2 plate 1808. Reference numeral 1809 denotes a photomask to be inspected; 1810, a stage; and 1811, a driving circuit for the stage 1810. The photomask 1809 is moved within a plane perpendicular to the beam 1806 by the stage 1810 and the driving circuit 1811 therefor. Reference numeral 1812 denotes a half mirror for superposing the beams 1805 and 1806 on each other; 1813, a rotatable analyzer; 1814, a light intensity detector; and 1815, a control computer; and 1816, an optical path adjusting apparatus. Assume that the polarization direction of the beam 1806 is the x direction, and the polarization direction of the beam 1805 passing through the λ/2 plate 1808 is the y direction, in this case, the two beams 1805 and 1806 can be expressed in the same manner as in the embodiment shown in FIG. 23.

The stage 1810 is controlled to move to a position where a pattern of interest on the photomask 1809 is superposed on the beam 1806, and is stopped at the position. A phase delay $\delta_y$ of the beam 1805 at the half mirror 1812 is adjusted by the optical path adjusting apparatus 1816 to set $\delta$ in equation (4) to be 0 or $2\pi$. In this case, as is apparent from equation (3), polarized light produced when the beams 1805 and 1806 are superposed on each other by the half mirror 1812 becomes linearly polarized light. The analyzer 1813 is fixed in a direction perpendicular to the polarization direction of the linearly polarized light produced upon superposition. Subsequently, the stage 1810 is continuously moved. That is, the beam 1806 scans over the photomask 1809 from the view point of the photomask 1809. When a properly formed pattern of interest comes to the position of the beam 1806, no light is incident on the light intensity detector 1814. For this reason, an output from the light intensity detector 1814 is 0. If improperly formed pattern of interest or a pattern other than the pattern of interest comes to the position of the beam 1806, light is incident on the light intensity detector 1814. If, therefore, a portion corresponding to output "0" from the light intensity detector 1814 is displayed, only the properly formed pattern of interest is imaged. A defect can be detected by comparing the shape of an actually formed pattern of interest with that of a design pattern of interest.

Figure 25:
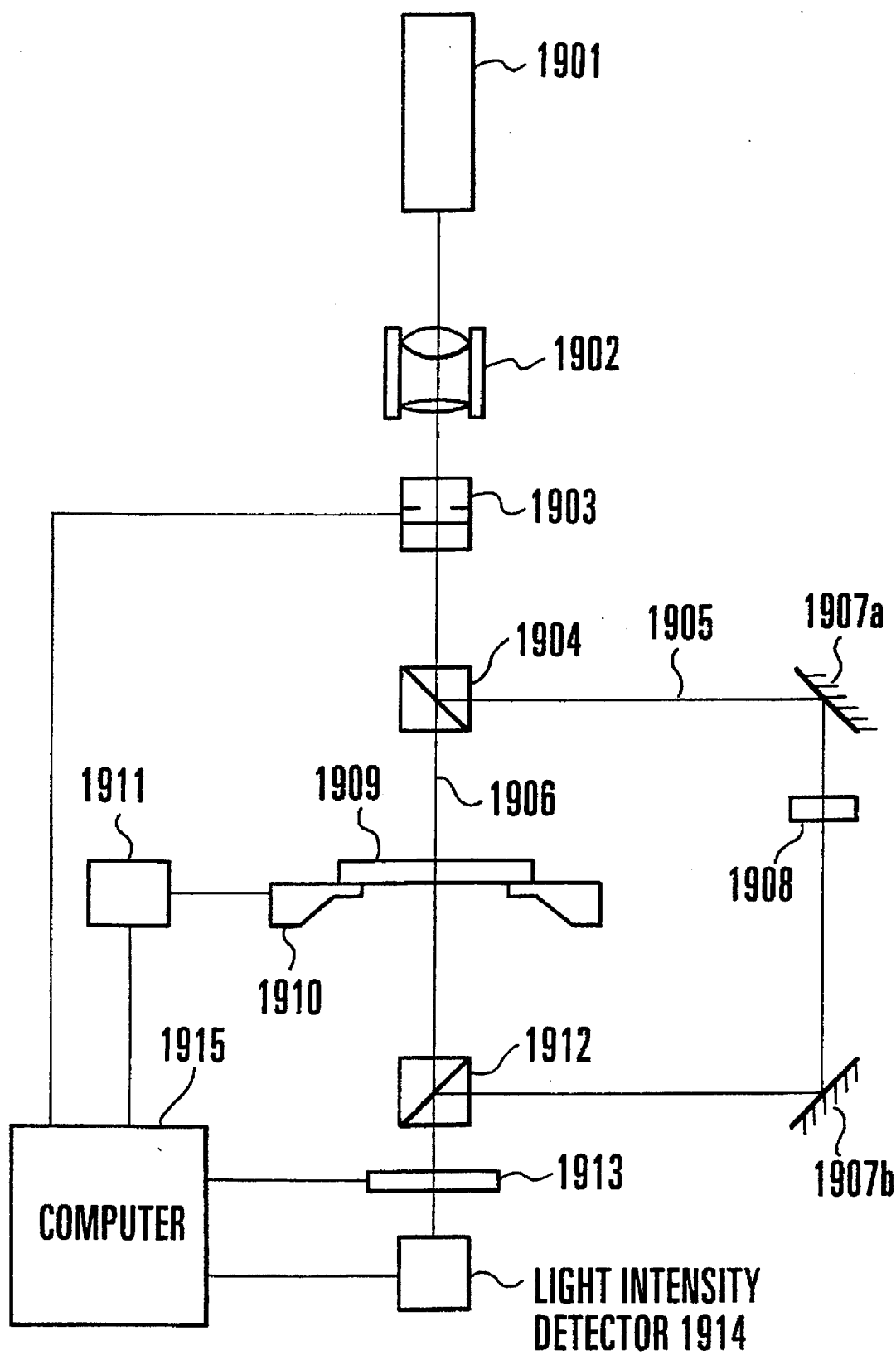

FIG. 25 shows still another embodiment of the present invention. Referring to FIG. 25, reference numeral 1901 denotes a laser for emitting polarized light; 1902, an enlargement/reduction optical system; 1903, a beam shaping system; and 1904, a beam splitter. A laser beam emitted, as a linearly polarized beam, from the laser 1901 becomes a beam having a large cross-sectional area by the enlargement/reduction optical system 1902. The beam is shaped to have a rectangular cross-sectional shape by the beam shaping system 1903. The beams is then split into beams propagating along two optical paths by the beam splitter 1904. Reference numerals 1905 and 1906 denote split beams; 1907a and 1907b, total reflection mirrors; 1908, a λ/2 plate for rotating the polarization plane of the beam 1905 in a direction perpendicular to the beam 1906; 1909, a photomask to be inspected; 1910, a stage; and 1911, a driving circuit for the stage 1910. The photomask 1909 is moved within a plane perpendicular to the beam 1906 by the driving circuit 1911. Reference numeral 1912 denotes a half mirror for superposing the beams 1905 and 1906 on each other; 1913, a rotatable analyzer; 1914, a light intensity detector; and 1915, a control computer. Assume that the polarization direction of the beam 1906 is the x direction, and the polarization direction of the beam 1905 passing through the λ/2 plate 1908 is the y direction. In this case, the two beams 1905 and 1906 can be expressed in the same manner as in the embodiment shown in FIG. 23. Therefore, δ" and $a_x$" are obtained first before the photomask 1909 is set on the stage 1910. In this case, since $a_x$" is dependent on the cross-sectional area of the beam 1906, $a_x$" is stored as an amount per unit cross-sectional area, in the control computer 1915. The photomask 1909 is then set on the stage 1910. The control computer 1915 issues a command to the driving circuit 1911 to control the stage 1910 so as to superpose a measurement start portion of the photomask 1909 on the beam 1906, and stops the stage 1910 at the corresponding position. At this time, since the shape of the pattern of interest superposed on the beam 1906 can be known by the control computer 1915, the beam shaping system 1903 is controlled by the control computer 1915 to shape the beam to have the same cross-sectional shape as that of the pattern of interest. Thereafter, δ and $a_x$ are obtained. With regard to $a_x$, an amount per unit cross-sectional area is calculated. The values of δ and T are calculated on the basis of these values according to equations (40) and (41). Subsequently, the control computer 1915 issues a command to the driving circuit 1911 to control the stage 1910 so as to superpose the next measurement portion of the photomask 1909 on the beam 1906, and stops the stage 1910 at the corresponding position. The beam shaping system 1903 is controlled to make the pattern (of interest) superposed on the beam 1906 coincide with the cross-sectional shape of the beam 1906. Thereafter, δ and $a_x$ are obtained. With regard to $a_x$, an amount per unit cross-sectional area is calculated. The values of θ and T are calculated according to equations (40) and (41).

By repeating the above procedures, the transmittance distribution and phase change amount distribution of the photomask 1909 are obtained. Defects and the like caused by factors in the manufacturing of the photomask 1909 can be known by comparing the design transmittance distribution and design phase change amount distribution of the photomask 1909 with the distributions actually obtained in the present invention. Assume that a predetermined range is set with respect to transmittances or phase change amounts, and only a portion exhibiting a measurement value falling within the range is displayed. In this case, only a pattern of a phase or transmittance of interest can be imaged.

In the embodiment shown in FIG. 25, the beam shaping system forms a beam having a rectangular cross-sectional shape. If a pattern of interest which is superposed on the beam 1906 is not rectangular, the pattern of interest may be divided into rectangular portions. Alternatively, the beam shaping System 1903 may be designed such that cells such as liquid crystal cells are arranged within a two-dimensional plane, and the transmittance of each cell can be changed in accordance with an external signal. With this beam shaping system, the beam 1906 can be shaped to have a cross-sectional shape coinciding with the shape of a pattern of interest.

As described above, according to the embodiments shown in FIGS. 23 to 25, the transmittance and phase change amount of each photomask portion can be easily and accurately obtained. In addition, since only a specific pattern can be imaged, or an image having the specific pattern emphasized can be formed, the shape of the specific pattern can be inspected. Furthermore, if the thickness of an object is a known value, the refractive index and absorption coefficient or extinction coefficient of the object can be obtained from the obtained amplitude transmittance and phase change amount.

What is claimed is:

1. An elliptical light measuring method comprising the steps of:

causing elliptical light which is to be measured to be incident on an analyzer while rotating said analyzer about an optical axis of the elliptical light, thereby obtaining a maximum light intensity of polarized light emerging from said analyzer, a rotational angle of said analyzer which corresponds to the maximum light intensity, and a minimum light intensity of the polarized light;

setting a λ/4 plate on an incident side of said analyzer, and rotating said analyzer about the optical axis of the elliptical light while sequentially causing the elliptical light to be incident on said λ/4 plate and said analyzer, thereby obtaining a rotational angle of said analyzer when a light intensity of polarized light emerging from said analyzer is maximized; and determining a polarized state of the elliptical light on the basis of four values, namely the maximum light intensity, the rotation angle of said analyzer which corresponds to the maximum light intensity, the minimum light intensity, and the rotational angle of said analyzer which corresponds to the maximum light intensity when said λ/4 plate is inserted.

* * * * *

UNITED STATES PATENT AND TRADEMARK OFFICE
CERTIFICATE OF CORRECTION

```
PATENT NO.   : 5,661,560
DATED        : August 26, 1997
INVENTOR(S)  : Ozaki Yoshiharu
```

It is certified that error appears in the above-indentified patent and that said Letters Patent is hereby corrected as shown below:

```
On the Title page of the patent, item [73] Assignee: should be listed as:
NIPPON TELEGRAPH AND TELEPHONE CORPORATION, Japan
```

Signed and Sealed this

Sixteenth Day of December, 1997

*Attest:*

BRUCE LEHMAN

*Attesting Officer*      *Commissioner of Patents and Trademarks*